United States Patent
de Abreu Pinho et al.

(10) Patent No.: US 11,762,752 B2
(45) Date of Patent: *Sep. 19, 2023

(54) FACILITATING DETECTION OF ANOMALIES IN DATA CENTER TELEMETRY

(71) Applicant: EMC IP Holding Company LLC, Hopkinton, MA (US)

(72) Inventors: Rômulo Teixeira de Abreu Pinho, Niteroi (BR); Vitor Silva Sousa, Niteroi (BR); Rodrigo Rios Almeida de Souza, Rio de Janeiro (BR); Roberto Nery Stelling Neto, Rio de Janeiro (BR)

(73) Assignee: EMC IP HOLDING COMPANY LLC, Hopkinton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/725,055

(22) Filed: Apr. 20, 2022

(65) Prior Publication Data

US 2022/0253370 A1 Aug. 11, 2022

Related U.S. Application Data

(63) Continuation of application No. 16/734,838, filed on Jan. 6, 2020, now Pat. No. 11,341,026.

(51) Int. Cl.
*G06F 11/00* (2006.01)
*G06F 11/34* (2006.01)
(Continued)

(52) U.S. Cl.
CPC .......... *G06F 11/3409* (2013.01); *G06F 11/22* (2013.01); *G06F 11/2263* (2013.01);
(Continued)

(58) Field of Classification Search
CPC ... G06F 11/3452; G06F 11/3065; G06F 11/30
See application file for complete search history.

(56) References Cited

U.S. PATENT DOCUMENTS 10,444,032 B2 * 10/2019 Takahashi ............... G06F 17/18
10,467,067 B2 * 11/2019 Patton ................... H04L 9/3297
(Continued)

OTHER PUBLICATIONS

Non-Final Office Action received for U.S. Appl. No. 16/861,982 dated Sep. 14, 2021, 21 pages.
(Continued)

*Primary Examiner* — Amine Riad
(74) *Attorney, Agent, or Firm* — Amin, Turocy & Watson, LLP

(57) ABSTRACT

Facilitating detection of anomalies of a target entity is provided herein. A system can comprise a processor and a memory that stores executable instructions that, when executed by the processor, facilitate performance of operations. The operations can comprise training a model on a first set of variables that are constrained by a second set of variables. The second set of variables can characterize elements of a defined entity. The first set of variables can define a normality of the defined entity. The operations also can comprise employing the model to identify expected parameters and unexpected parameters associated with the defined entity to at least a defined level of confidence.

20 Claims, 15 Drawing Sheets

(51) Int. Cl.
*G06N 20/00* (2019.01)
*G06F 11/30* (2006.01)
*G06F 11/22* (2006.01)
*G06F 18/22* (2023.01)
*G06F 18/24* (2023.01)

(52) U.S. Cl.
CPC .......... *G06F 11/30* (2013.01); *G06F 11/3065* (2013.01); *G06F 11/3452* (2013.01); *G06F 11/3495* (2013.01); *G06F 18/22* (2023.01); *G06F 18/24* (2023.01); *G06N 20/00* (2019.01)

(56) References Cited

U.S. PATENT DOCUMENTS

| | | | |
|---|---|---|---|
| 10,630,561 B1* | 4/2020 | Tao | H04L 43/0888 |
| 10,956,808 B1* | 3/2021 | Bhardwaj | G06N 3/045 |
| 10,997,009 B2* | 5/2021 | Poghosyan | G06F 11/079 |
| 2010/0241615 A1* | 9/2010 | Marshall | G06F 16/116 |
| | | | 707/661 |
| 2012/0059779 A1 | 3/2012 | Syed et al. | |
| 2012/0226823 A1* | 9/2012 | Livnat | G06F 21/6209 |
| | | | 709/246 |
| 2017/0102693 A1* | 4/2017 | Kidd | G05B 19/41875 |
| 2017/0102694 A1* | 4/2017 | Enver | G05B 19/4184 |
| 2017/0102696 A1* | 4/2017 | Bell | G05B 23/0275 |
| 2019/0133536 A1* | 5/2019 | Roberts | G16H 50/30 |
| 2019/0147670 A1* | 5/2019 | Chopra | G05B 23/0243 |
| | | | 701/29.1 |
| 2019/0149440 A1* | 5/2019 | Rantzau | H04L 43/045 |
| | | | 370/241 |
| 2019/0205232 A1* | 7/2019 | Ayyagari | G06F 11/2205 |
| 2019/0213198 A1* | 7/2019 | Kannan | G06F 16/254 |
| 2019/0243739 A1* | 8/2019 | Song | G06F 11/0793 |
| 2019/0294642 A1* | 9/2019 | Matlick | G06F 16/958 |
| 2021/0034949 A1* | 2/2021 | Singh | G06N 3/044 |
| 2021/0150261 A1* | 5/2021 | Zhang | G06N 3/08 |
| 2021/0208995 A1* | 7/2021 | de Abreu Pinho | G06N 5/045 |

OTHER PUBLICATIONS

Aggarwal et al., "Outlier Analysis," Springer, 2017.
Aggarwal et al., "Data Clustering: Algorithms and Applications," Chapman\& Hall/CRC, 2013.
Bagnall et al., "The great time series classification bake off: a review and experimental evaluation of recent Algorithmic advances," Data Min Knowl Disc, vol. 31, pp. 606-660, 2017.
Schutze et al., "Foundations of Statistical Natural Language Processing", Cambridge, Mass: MIT Press, 2006.
Allison, "Missing Data", SAGE Publications, 2001, 97 pages.
Non-Final Office Action received for U.S. Appl. No. 16/734,838 dated Sep. 16, 2021, 26 pages.
Final Office Action received for U.S. Appl. No. 16/861,982 dated Feb. 9, 2022, 31 pages.

* cited by examiner

FACILITATING DETECTION OF ANOMALIES IN DATA CENTER TELEMETRY

RELATED APPLICATION

The subject patent application is a continuation of, and claims priority to, U.S. patent application Ser. No. 16/734,838 (now U.S. Pat. No. 11,341,026), filed Jan. 6, 2020, and entitled "FACILITATING DETECTION OF ANOMALIES IN DATA CENTER TELEMETRY," the entirety of which application is hereby incorporated by reference herein.

TECHNICAL FIELD

The subject disclosure relates generally to data storage systems and communications. More specifically, the subject disclosure relates to anomaly detection of such systems.

BACKGROUND

Anomaly detection systems are used to detect anomalies in a data center (e.g., a storage system) by monitoring its computing, network, and storage systems and establishing normal behavior of the data center. If any system is outside what has been established as normal ranges at any given time, the monitoring system can trigger warnings or correction policies to circumvent the abnormal behavior. A main difficulty for the detection of anomalies in data center operations is the overwhelming number of variables to monitor. For example, a single storage system can contain of a cluster with tens of nodes, each node collecting data for more than a hundred variables. Accordingly, it can be nearly impossible to identify the important variables to monitor.

The above-described context with respect to conventional anomaly detection systems is merely intended to provide an overview of current technology and is not intended to be exhaustive. Other contextual description, and corresponding benefits of some of the various non-limiting embodiments described herein, can become further apparent upon review of the following detailed description.

SUMMARY

The following presents a simplified summary of the disclosed subject matter to provide a basic understanding of some aspects of the various embodiments. This summary is not an extensive overview of the various embodiments. It is intended neither to identify key or critical elements of the various embodiments nor to delineate the scope of the various embodiments. Its sole purpose is to present some concepts of the disclosure in a streamlined form as a prelude to the more detailed description that is presented later.

In an embodiment, provided herein is a method that can comprise training, by a system comprising a processor, a model on a first set of variables that are constrained by a second set of variables. The second set of variables can characterize elements of a defined entity. The first set of variables can define a normality and an anomaly of the defined entity. Further, the method can comprise employing, by the system, the model to identify a normal state or an anomalous state of the defined entity to at least a defined level of confidence.

According to some implementations, the method can comprise transforming, by the system, the second set of variables associated with the defined entity into a derivative representation that comprises the first set of variables for the defined entity. The method also can comprise detecting, by the system, an anomaly of the defined entity based on the first set of variables. The second set of variables can provide context for a definition of normality and a detection of anomalies associated with the defined entity. Further to the above implementations, the method can comprise prior to detecting the anomaly, constraining, by the system, the first set of variables based on the derivative representation of the second set of variables.

In alternative or additional implementations, transforming the second set of variables can comprise grouping elements of the defined entity based on a similarity function. Further, the similarity function can be based on a pairwise similarity between the elements of the defined entity. The pairwise similarity can be based on combining, by the system, variables of different natures of the second set of variables into a single weighted similarity function. In an example, the variables of different natures can comprise configuration variables of the elements of the defined entity and conditions of usage variables of the elements of the defined entity.

Further to the above alternative or additional implementations, the method can comprise assessing, by the system, the first set of variables associated with normal behavior to a group to which the first set of variables belong. The method also can comprise classifying, by the system, a test sample as normal or anomalous based on the assessing. In an example, the first set of variables can comprise performance variables.

Another embodiment relates to a system that can comprise a processor and a memory that stores executable instructions that, when executed by the processor, facilitate performance of operations. The operations can comprise training a model on a first set of variables that are constrained by a second set of variables. The second set of variables can characterize elements of a defined entity. The first set of variables can define a normality of the defined entity. The operations also can comprise employing the model to identify expected parameters and unexpected parameters associated with the defined entity to at least a defined level of confidence.

In accordance with some implementations, the operations also can comprise transforming the second set of variables into a representation that comprises the first set of variables. Further, the operations can comprise performing anomaly detection of the defined entity based on the first set of variables. The first set of variables can provide context for a definition of normality and a detection of anomalies associated with the defined entity. In an example, transforming the second set of variables can comprise constraining the first set of variables based on a derivative representation of the second set of variables.

Further, in some implementations, the operations can comprise evaluating performance variables associated with normal behavior of the defined entity to a group to which the second set of variables belong. The operations also can comprise classifying a test sample as normal or anomalous based on result of the evaluating.

In an example, transforming the second set of variables can comprise grouping elements of the defined entity based on a similarity function. Further to this example, the operations can comprise combining, by the system, variables of different natures of the second set of variables into a single weighted similarity function, resulting in a pairwise similarity. The similarity function can be based on the pairwise similarity between the elements of the defined entity. The variables of different natures can comprise configuration variables of the elements of the defined entity and conditions of usage variables of the elements of the defined entity.

Another embodiment relates to a system that can comprise a processor and a memory that stores executable instructions that, when executed by the processor, facilitate performance of operations. The operations can comprise training a model on a first group of variables that are constrained by a second group of variables. The second group of variables can characterize elements of a defined entity. The first group of variables can define a normality and an anomaly of the defined entity. Further, the operations can comprise employing the model to identify a normal state or an anomalous state of the defined entity to a defined level of confidence.

According to some implementations, the operations can comprise transforming the second group of variables associated with the defined entity into a derivative representation that comprises the first group of variables for the defined entity. In addition, the operations can comprise detecting an anomaly of the defined entity based on the first group of variables. The second group of variables can provide context for a definition of normality and a detection of anomalies associated with the defined entity. Further, the operations can comprise constraining the first group of variables based on the derivative representation of the second group of variables.

In another example, the operations can comprise grouping elements of the defined entity based on a similarity function. The similarity function can be based on a pairwise similarity between the elements of the defined entity. The pairwise similarity can be based on a combination of variables of different natures of the second group of variables into a single weighted similarity function. In addition, the variables of different natures can comprise configuration variables of the elements of the defined entity and conditions of usage variables of the elements of the defined entity.

To the accomplishment of the foregoing and related ends, the disclosed subject matter comprises one or more of the features hereinafter more fully described. The following description and the annexed drawings set forth in detail certain illustrative aspects of the subject matter. However, these aspects are indicative of but a few of the various ways in which the principles of the subject matter can be employed. Other aspects, advantages, and novel features of the disclosed subject matter will become apparent from the following detailed description when considered in conjunction with the drawings. It will also be appreciated that the detailed description can include additional or alternative embodiments beyond those described in this summary.

BRIEF DESCRIPTION OF THE DRAWINGS

Various non-limiting embodiments are further described with reference to the accompanying drawings in which.

DETAILED DESCRIPTION

Figure 1:
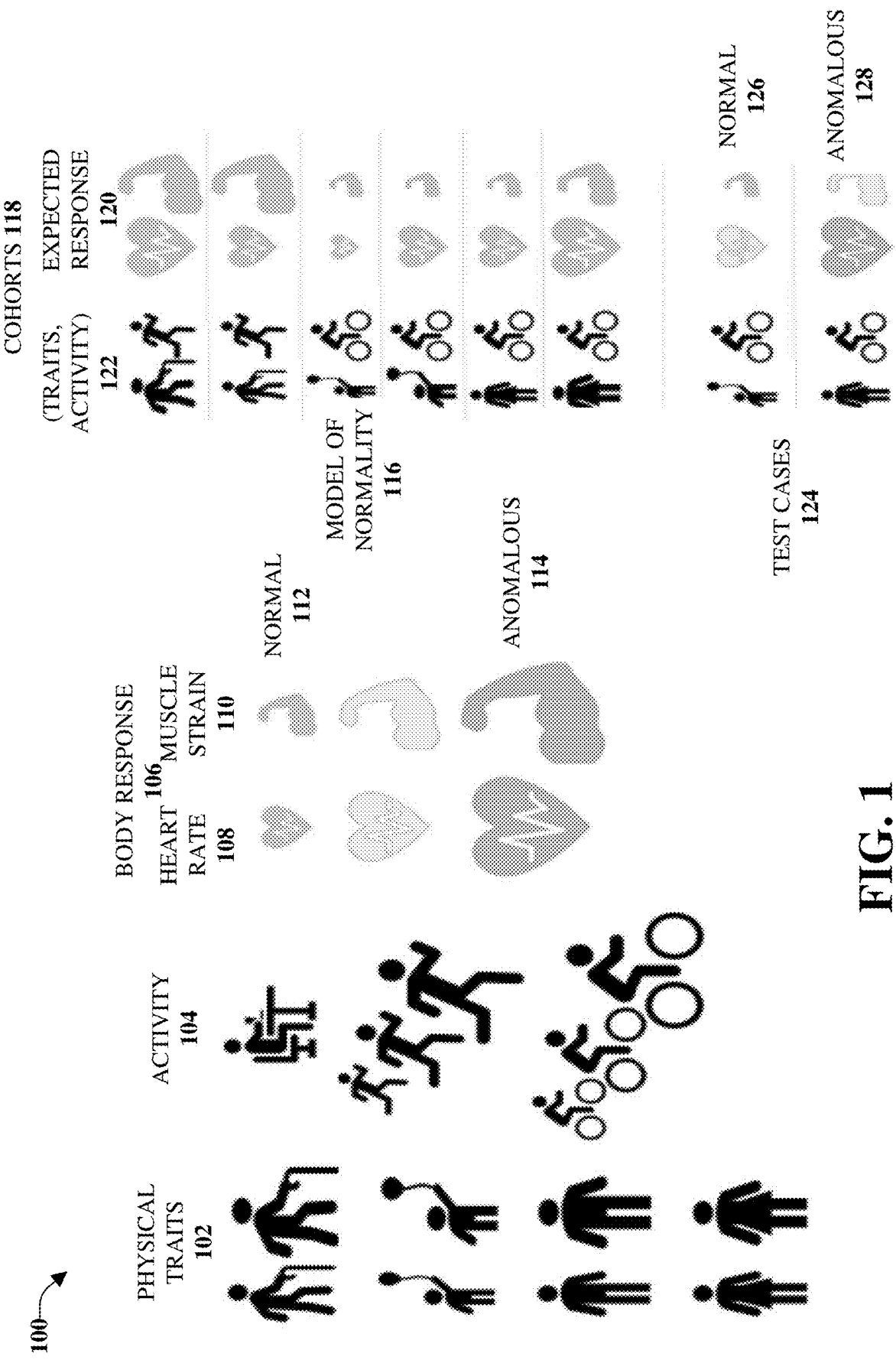
FIG. 1 illustrates an example, non-limiting, representation of identification of anomalous cases in medical studies using cohorts.

One or more embodiments are now described more fully hereinafter with reference to the accompanying drawings in which example embodiments are shown. In the following description, for purposes of explanation, numerous specific details are set forth in order to provide a thorough understanding of the various embodiments. However, the various embodiments can be practiced without these specific details. In other instances, well-known structures and devices are shown in block diagram form in order to facilitate describing the various embodiments.

Anomaly detection systems can be applied in contexts with inherent complexity and large volumes of data, such as data center management, industrial applications, and in financial scenarios. In data center management and resource administration, for example, neglecting anomalies can lead to malfunction, failures, and/or suboptimal allocation of computational resources. All these problems ultimately can result in financial loss and long-term operational problems. Therefore, properly detecting anomalies can empower the derivation of an action plan for each state of interest, either by preventing a disruptive effect from subsequent states, triggering self-tuned policies to handle such events, or acting in a timely manner to diminish losses.

As mentioned, to detect anomalies in a data center, its computing, network and storage systems are monitored, and its normal behavior is established from any collected data. If any system is outside what has been established as normal ranges at any given time, the monitoring application can trigger warnings or correction policies to circumvent the abnormal behavior. A main difficulty for the detection of anomalies in data center operations is the overwhelming number of variables to monitor. For example, a single storage system can contain a cluster with tens of nodes, each node collecting data for more than a hundred variables. Identifying the important variables to monitor can make the anomaly detection problem more tractable and thus provide some guidance for the challenging process of finding its root causes.

The various aspects disclosed herein can categorize system variables and selectively combine the system variables to improve the accuracy of the anomaly detection process. The disclosed aspects can also make the system variables more intuitive in large multi-dimensional data center telemetry. With the disclosed aspects, an extra-exogenous approach is defined that uses a set of variable categories to characterize systems and another set of variable categories that is used to detect anomalies based on the expected normal behavior of a system having certain characteristics. Such separation allows anomaly detection models and associated systems to focus on the more important variables to monitor.

Conventionally, the issue of detecting anomalous behaviors in data centers poses various challenges. For example, data centers have hundreds of variables that can be monitored for the occurrence of anomalies. With such a large number of variables, the problem is generally affected by the curse of dimensionality. As a result, detecting the anomalies and understanding their root causes become a cumbersome task.

There are many options and methods that can be used to reduce the dimensionality of the data, such as Principal Components Analysis (PCA) and auto-encoders. However, these methods tend to reduce the interpretability of the results. Another option is correlation analysis, which allows the removal of variables that have a strong linear correlation with other variables. Despite being effective in many cases, correlation analysis is only effective for variable removal when the variables have the expected high-collinearity.

Therefore, in situations where many variables must be used in a model, it is important to identify which of the variables are the most relevant to analyze and which variables, ultimately, facilitate the anomaly detection process. In other words, it is important to identify the target variables of the anomaly detection model.

Endogenous and exogenous definitions of normality will now be discussed. Data center telemetry generally appears in the form of time-series. In anomaly detection via conventional time-series analysis, a prediction model of normality indicates the expected values of the target variables being monitored based on past data. The model defines a range of normality for the prediction and classifies samples as anomalous if they are outside the normal ranges.

Let y be the target variable and $\hat{y}$ be the estimate of y obtained from a prediction model with parameters θ. The prediction model is endogenous when past values of the target variables themselves are used to predict their future (normal) values. Namely, $\hat{y}=f(y|\theta)$. It is exogenous when other variables, x, referred to as predictors, predict the target variables. Namely, $\hat{y}=f(x|\theta)$. In effect, most conventional methods address anomaly detection problems in time-series via endogenous or exogenous models.

Nevertheless, the definition of normality in data center telemetry might go beyond the endogenous versus exogenous paradigm. For example, while a certain variable can be outside its normal range from an endogenous perspective (e.g., considering its own past), it might still be normal from a more general view of the system, which would not characterize an observed sample value as anomalous. Conversely, normal readings of telemetry variables from an exogenous perspective could otherwise have been classified as anomalous if they had been observed in a more restricted context. Therefore, a model that can identify anomalies in both scenarios has been a long-felt need and is provided by the disclosed aspects.

The disclosed aspects facilitate the detection of anomalies in data center telemetry via an extra-exogenous, multi-dimensional model of normality to classify data center system elements as being in a normal state or in an anomalous state. According to the disclosed model, a first set of variables can be used to characterize elements in the data center (e.g., compute, storage or network). Alone, such set would generally define an endogenous method to detect anomalies. However, as discussed herein, a second set of variables is used to define normality, constraining such set by the first one (e.g., the first set).

Accordingly, the disclosed aspects can transform the predictors into another representation, $z=f(x|\theta x)$, and associate the target variables y and estimate the target variables $\hat{y}$ from that representation. Namely, $\hat{y}=g(z|\theta z)$. This relationship between the first and second sets of variables, for example, x and z, is what can be utilized to identify the disclosed aspects as an extra-exogenous model for anomaly detection. The other representation can be a secondary representation (or a derivative representation). The following provides some intuition behind the disclosed aspects and describes its technical details.

For purposes of explanation and not limitation, to make the extra-exogenous concept clearer an analogy with medical studies is now provided. In this analogy, individuals are grouped into cohorts sharing common features or aspects of behavior. Depending on the study, such cohorts have expected responses under certain conditions. This concept is illustrated in FIG. 1, which is an example, non-limiting, representation 100 of identification of anomalous cases in medical studies using cohorts.

In FIG. 1 individuals can be characterized by physical traits 102 such as gender, age, and weight, although other physical traits could be utilized to characterize the individuals. When performing certain activities 104, such as sitting and running or cycling at different speeds, the individuals' bodies response 106 in terms of, for example, heart rate 108 and muscle strain 110 can be different from one another.

The information above can be used to classify whether an individual's body responds to the referred activities in a normal 112 or an anomalous 114 way. There is no "one-size-fits-all" answer to this question. In effect, normal or abnormal depends on the individual's physical traits and on the activity under consideration. Therefore, a model of normality 116 should capture the expected body responses for specific cohorts 118. Only after identifying to which cohort an individual belongs can it be inferred whether his or her body's response is within the normal ranges for the cohort.

As mentioned, in FIG. 1 individuals are grouped according to their physical traits and to the conditions of the activity they are performing. Each group has an expected response 120 to the referred activity 122. Test cases 124 showing responses outside of the normal ranges 126 of the group to which they belong are considered anomalous 128.

Figure 2:
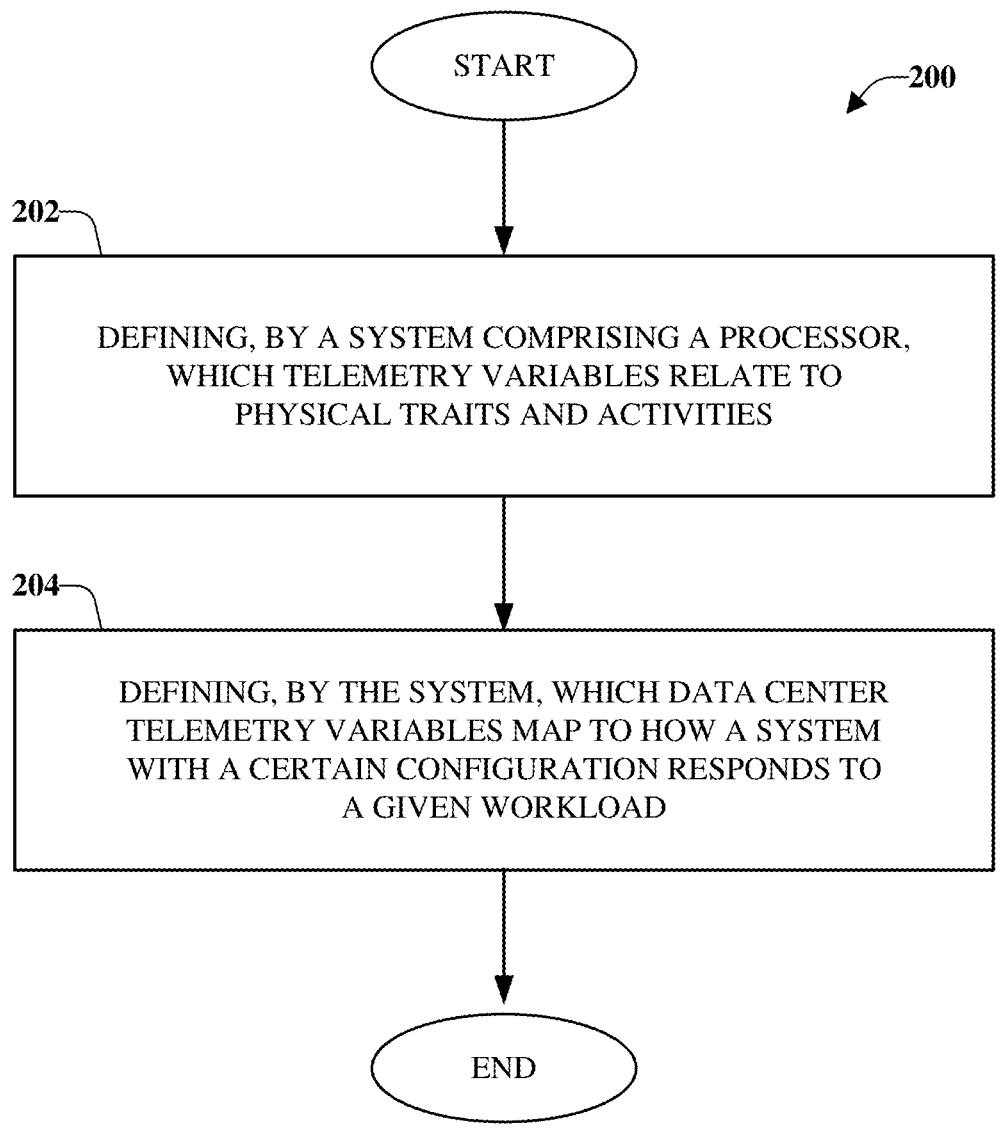
FIG. 2 illustrates a flow diagram of an example, non-limiting, computer-implemented method that facilitates creation of an anomaly detection model in accordance with one or more embodiments described herein.

FIG. 2 illustrates a flow diagram of an example, non-limiting, computer-implemented method 200 that facilitates creation of an anomaly detection model in accordance with one or more embodiments described herein. More specifically, the computer-implemented method 200 relates to how to apply the concepts discussed in the creation of an anomaly detection model and in the classification of test samples. Initially, groups can be created according to system configuration and workload characteristics.

To map the medical concepts (discussed above with respect to FIG. 1) to data center resources such as computing, storage, and networking devices telemetry, the computer-implemented method 200 begins, at 202, when a system comprising a processor, can defined which telemetry variables relate to physical traits and activities. Using domain knowledge, for example, a natural choice can be to use system configuration variables as surrogates for physical traits. Namely, variables such as the number of CPUs, disks, network interfaces, the amount of available memory, and so on, can be used to define the "physical traits" of a system. The workload variables, on the other hand, can define how the system is being used. In a Network Attached Storage (NAS), for example, variables such as the read and write throughputs, latency of an I/O operation, I/O Operations Per Second (IOPS), sequentially of the I/O patterns, number of connected clients per minute/hour/day, and so on, can provide information about the "activities" being executed on the system.

As discussed herein, groups (or cohorts) of data center elements can be created using a combination of workload and configuration characteristics. The creation of groups is the transformation $z=f(x|\theta')$ mentioned above. According to some implementations, clustering algorithms (such as K-Means, Density-based Spatial Clustering of Applications with Noise (DBSCAN), Hierarchical clustering, and so on) can group elements in a database using a measure of pairwise similarity between the group elements. Examples of similarity measures are the Euclidean and the Cosine distances, but other measures exist and could be utilized with the disclosed aspects.

According to some implementations, configuration and workload variables can be combined using a weighting factor $\alpha$. Given two samples of the database, $x=[cx,wx]T$ and $y=[cy,wy]T$, where $[c, w]$ are the configuration and workload variables, respectively, the similarity between $x$ and $y$, $d(x, y)$, can be computed as:

$$d(x, y) = \alpha * dw(x, y) + (1 - \alpha) * dc(x, y)$$

In the equation above, dc and dw capture the similarity components of configuration and workload, respectively. Since configuration and workload variables can have different natures, their similarity is measured via independent functions. The parameter $\alpha$ is application dependent.

Note that the disclosed aspects are agnostic about the underlying similarity functions employed in the grouping phase. The emphasis is on the data representation that allows the creation of a model that groups data center elements based on their configuration and workload characteristics.

Further, at 204 of the computer-implemented method 200, the system can define which data center telemetry variables map to how a system with a certain configuration responds to a given workload. In the end, those are the target variables that will indicate whether a sample is in a normal or an anomalous state. In a NAS system, for example, performance variables such as the average system CPU usage, I/O response times, and network response times can provide evidence of whether the system is behaving as expected under the given workload (e.g., having a normal response to the observed workload). The model of normality is thus based on the normal ranges of the performance variables being monitored.

Note that each performance variable can have its own normality range, but a model of normality can be defined for their combination also. The disclosed data representation allows both approaches. It is noted that normality is defined with respect to the performance variables after constraining the data by their configuration and workload counterparts. In other words, this provides a sense of context to the detection of anomalies.

Figure 3:
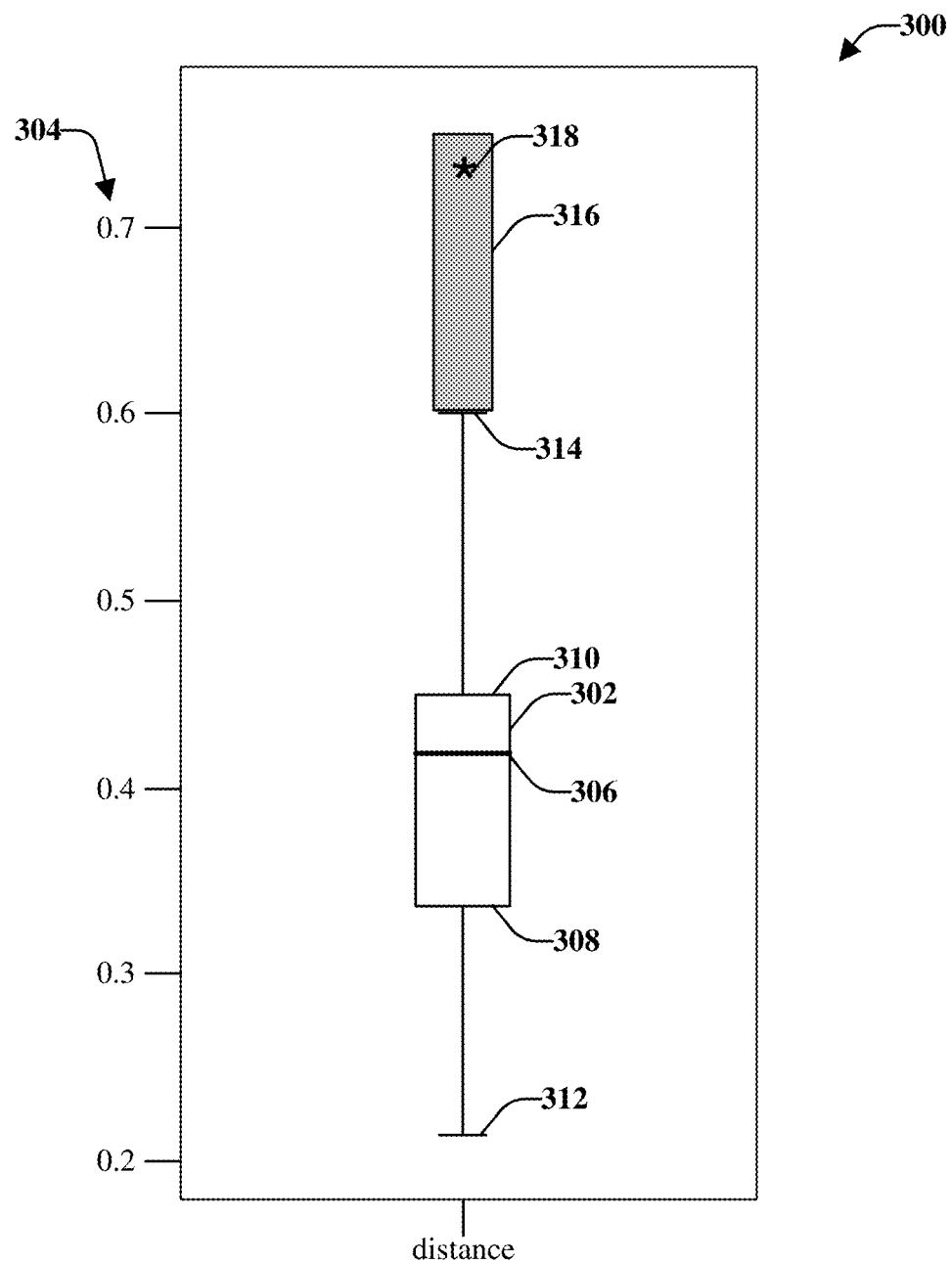
FIG. 3 illustrates an example, non-limiting, boxplot of an intra-group distance-to-centroid distribution for a test case in accordance with one or more embodiments described herein.

As an example, a simple method to define normality ranges for the combination of variables is to compute the centroid of all elements in a group and obtain the normal range of distances to the centroid. For example, FIG. 3 illustrates an example, non-limiting, boxplot of an intra-group distance-to-centroid distribution for a test case in accordance with one or more embodiments described herein. Specifically, FIG. 3 illustrates a model of normality 302 based on the distance to the centroid 304, which is indicated on the vertical axis. The example of FIG. 3 is for an anomalous test case. A normal range can be computed via an Inter-Quartile Range (IQR) of all distances computed for the group, as in FIG. 3.

The horizontal line represents the median 306 (e.g., 50th percentile), the bottom edge 308 represents the lower quartile, and the upper edge 310 represents the upper quartile. Further, the whiskers represent a lower extreme 312 and an upper extreme 314. An abnormal range 316 is also indicated, wherein the test case is plotted and indicates the test case as an outlier 318.

Assuming all performance variables, $p \in p$, are independent, another possible method is to compute their combined distribution as $\rho(p|c, w) = \Pi \rho(p|c, w) p \in p$ and to classify a sample as normal or anomalous depending on the probability of occurrence of the readings of its performance variables. Moreover, it is noted that the disclosed aspects are agnostic about the underlying heuristics for exposing the normality ranges.

Figure 4:
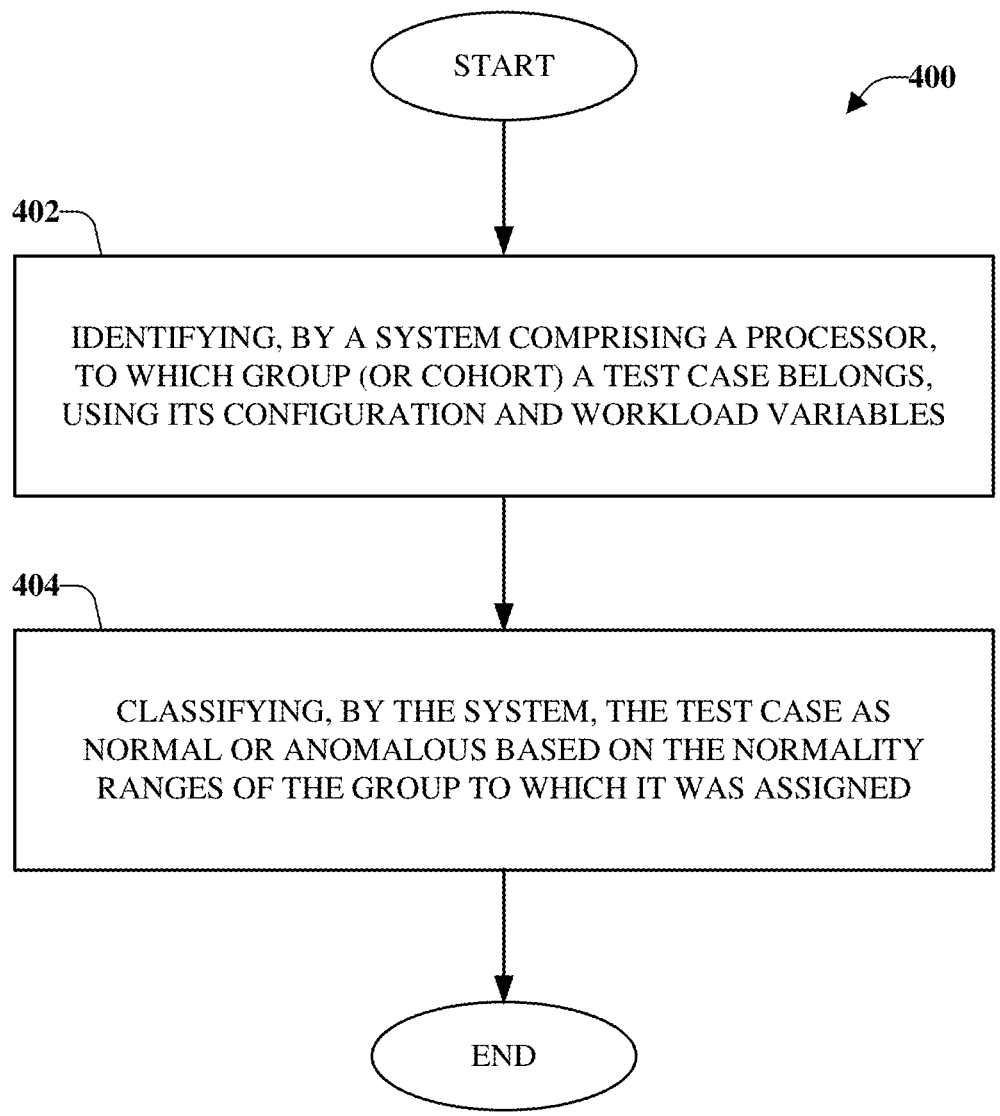
FIG. 4 illustrates a flow diagram of an example, non-limiting, computer-implemented method that facilitates classification of test cases in accordance with one or more embodiments described herein.

FIG. 4 illustrates a flow diagram of an example, non-limiting, computer-implemented method 400 that facilitates classification of test cases in accordance with one or more embodiments described herein. When classifying a test case, the computer-implemented method 400 starts, at 402, when a system comprising a processor, identifies to which group (or cohort) the test case belongs, using its configuration and workload variables. To do this, a similarity function, as discussed above, can be utilized. Considering the example distance-to-the-centroid approach described above, the test case can be associated with the group having the closest centroid. The 1-nearest-neighbor criterion can be also used in the domain of time-series classification. Again, the emphasis here is on the contextualization of a test case, which will constrain the ranges of normality to the ones related to the group to which the test case was assigned.

Figure 5:
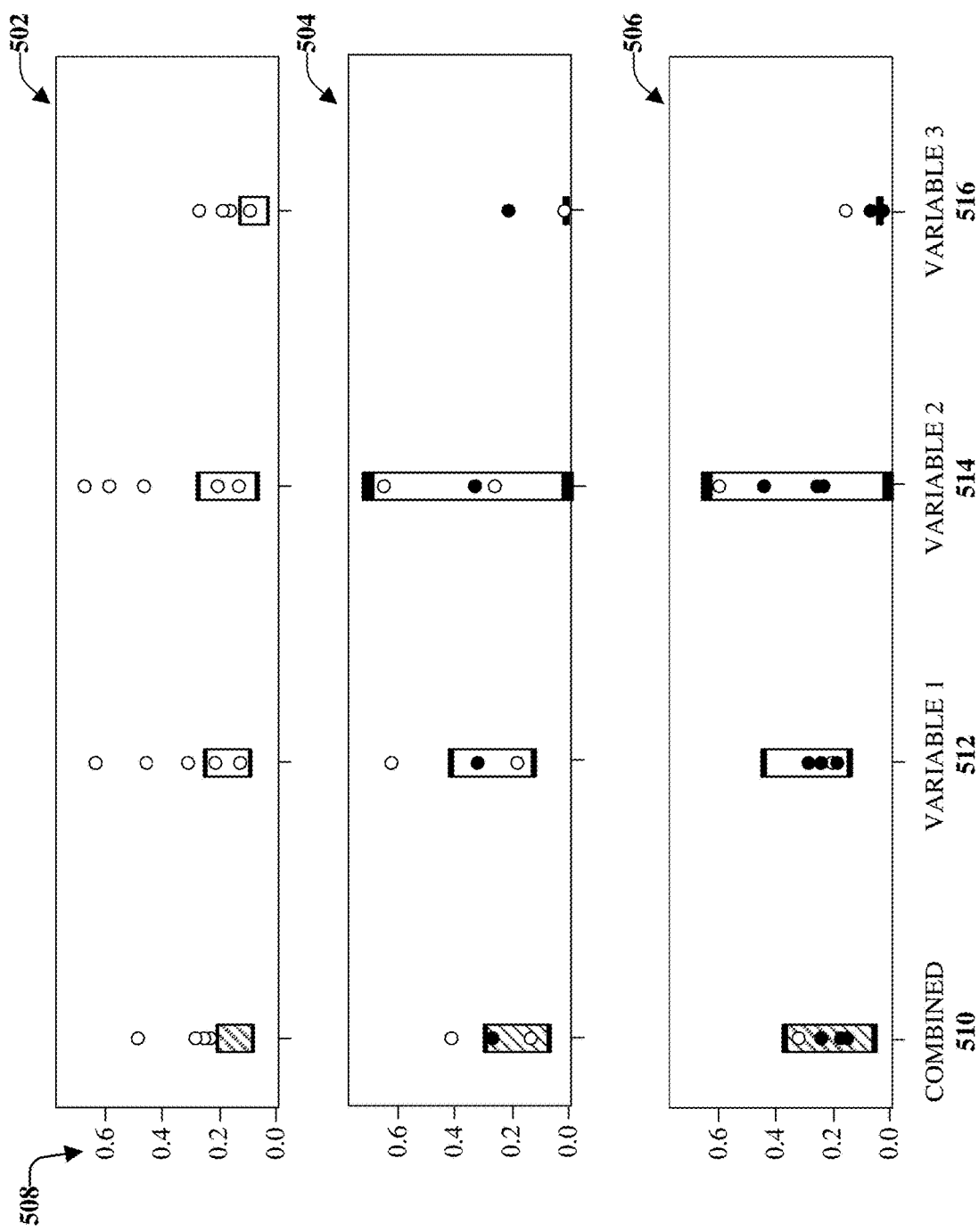
FIG. 5 illustrates non-limiting examples of boxplots for classifying test samples based on the normality ranges of performance variables and their combinations in accordance with one or more embodiments described herein.

Further, at 404 of the computer-implemented method 400, the test case can be classified as normal or anomalous based on the normality ranges of the group to which it was assigned. Again, assuming the distance-to-the-centroid criterion was used to define the normal ranges, a test case can be normal if the combination of the distances is within the normal ranges. FIG. 5 illustrates non-limiting examples of boxplots for classifying test samples based on the normality ranges of performance variables and their combinations in accordance with one or more embodiments described herein.

The first group of boxplots represents performance variables for a first group 502; the second group of boxplots represents performance variables for a second group 504; and the third group of boxplots represents performance variables for a third group 506. Distance to centroid 508 is represented on the vertical axis. The first boxplot in each group is a combination of variables 510, the second boxplot in each group is for a first variable 512, the third boxplot in each group is for a second variable 514, and the fourth boxplot in each group is for a third variable 516. The unshaded boxplots represent a normal range (per variable) and the shaded boxplots represent a normal range (combined). Further, the unshaded circles represent test cases (anomaly) and the shaded circles represent test cases (normal). As illustrated in FIG. 5, this approach also allows the identification of which variables appear to be anomalous and influenced the final classification results.

Figure 6:
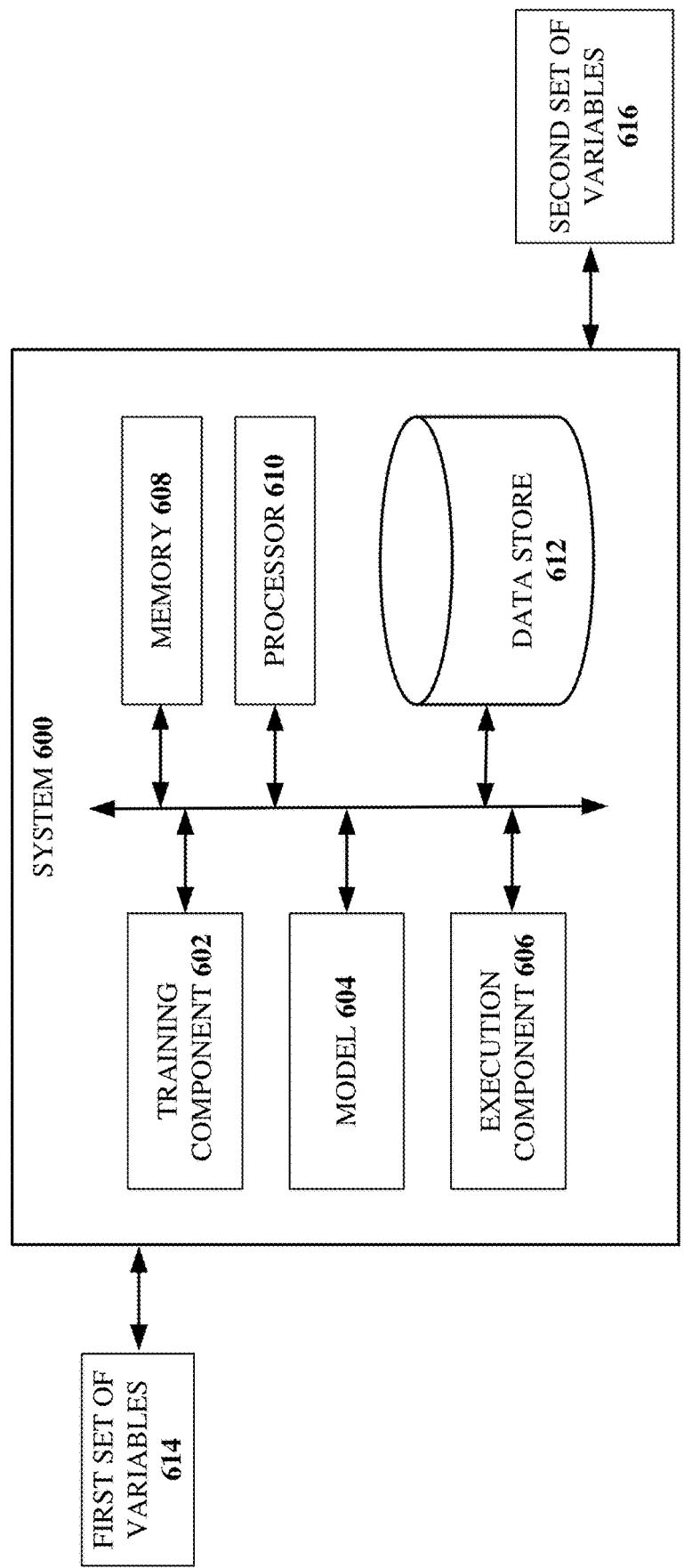
FIG. 6 illustrates a block diagram of an example, non-limiting, system for anomaly detection in accordance with one or more embodiments described herein.

FIG. 6 illustrates a block diagram of an example, non-limiting, system 600 for anomaly detection in accordance with one or more embodiments described herein. Aspects of systems (e.g., the system 600 and the like), apparatuses, and/or processes explained in this disclosure can constitute machine-executable component(s) embodied within machine(s) (e.g., embodied in one or more computer readable mediums (or media) associated with one or more machines). Such component(s), when executed by the one or more machines (e.g., computer(s), computing device(s), virtual machine(s), and so on) can cause the machine(s) to perform the operations described.

In various embodiments, the system 600 can be any type of component, machine, device, facility, apparatus, and/or instrument that comprises a processor and/or can be capable of effective and/or operative communication with a wired and/or wireless network. Components, machines, apparatuses, devices, facilities, and/or instrumentalities that can comprise the system 600 can include tablet computing devices, handheld devices, server class computing machines and/or databases, laptop computers, notebook computers, desktop computers, cell phones, smart phones, consumer appliances and/or instrumentation, industrial and/or commercial devices, hand-held devices, digital assistants, multimedia Internet enabled phones, multimedia players, and the like.

The system 600 (and the other embodiments described herein) can be utilized for anomaly detection. Anomaly detection systems are widely applied in contexts with inherent complexity and large volumes of data. In data center management and resource administration, neglecting anomalies can lead to malfunction, failures, and suboptimal allocation of computational resources. These problems ultimately result in financial loss and long-term operational problems. Therefore, properly detecting anomalies empowers development of an action plan for each state of interest. A difficulty for the detection of anomalies in data center operations is the overwhelming number of variables to monitor. Thus, identifying the most important variables to monitor can make the anomaly detection problem more tractable and thus provide guidance in the challenging process of finding its root causes. The system 600 can be configured to categorize system variables and combine the variables in such a way to improve the accuracy of the anomaly detection process and to make the detection process more intuitive in large multi-dimensional data center telemetry. As discussed herein, an extra-exogenous approach is defined that uses a set of variable categories to characterize systems and another set that is used to detect anomalies based on the expected normal behavior of a system having certain characteristics.

As illustrated, the system 600 can comprise a training component 602, a model 604, an execution component 606, at least one memory 608, at least one processor 610, and at least one data store 612. The training component 602 can train the model 604 on a first set of variables 614 that are constrained by a second set of variables 616. The second set of variables 616 can characterize elements of a defined entity. Further, the first set of variables 614 can define a normality of the defined entity.

As utilized herein an entity can be one or more computers, the Internet, one or more systems, one or more commercial enterprises, one or more computers, one or more computer programs, one or more machines, machinery, and so forth, hereinafter referred to as an entity or entities depending on the context.

The execution component 606 can employ the model 604 to identify expected parameters and unexpected parameters associated with the defined entity to a defined level of confidence. For example, the model 604 can be an extra-exogenous model for anomaly detection based on a relationship between the first set of variables 614 and the second set of variables 616.

According to some implementations, the second set of variables 616 can characterize elements of the defined entity, and the first set of variables 614 can define the normality of the defined entity. In a specific, non-limiting example, the second set of variables 614 can be characterization elements of a data center (e.g., the target entity is the data center), however, the disclosed aspects are not limited to this implementation.

The system 600, as well as other embodiments discussed herein, can provide an extra-exogenous model of normality. In an example, data center information technology resources telemetry can contain data from different natures. Therefore, detecting the anomalies and understanding their root causes can become a very difficult task. Accordingly, the various aspects provided can perform a transformation of predictor variables into a secondary representation, which constrains the target variables. By doing this, the model can concentrate on the most relevant variables to detect anomalies and define a more interpretable relationship between predictors and target variables.

Further, the system, as well as other embodiments discussed herein, can provide separation between configuration, workload and performance variables. To facilitate the operation of the various embodiments, predictors and target variables can be properly identified. This definition can be automatic and/or performed based on domain knowledge. In the case of anomaly detection in data centers, variables can be separated into configuration, workload, and performance categories (or other categories), using domain knowledge. In this separation, configuration and workload variables can be the predictors, which can define the physical traits of the data center system elements and how the elements are used. Performance variables can define how system elements with certain traits respond to a given workload. Configuration and workload variables can constrain the performance variables, which are the target variables used to detect anomalies.

Also provided herein is characterization of system elements based on configuration and workload variables. For example, configuration and workload variables can be employed to group data center information technology systems sharing similar "physical traits" (e.g., configuration) and being used under similar conditions (e.g., workload). This grouping is the transformation discussed herein, which defines the extra-exogenous aspects.

In addition, such groupings can employ a measure of pairwise similarity between data center elements, which combines variables of different natures into a single, weighted similarity function. For example, configuration and workload variables can be combined into a single similarity function, and the contribution of each variable category can be determined by a weighting factor, which is application dependent.

Classification of system elements from normality models are also provided herein. For example, discussed is the classification of data center elements as being in a normal or anomalous state. This can be facilitated by identifying to which group a test sample belongs, using the similarity function that combines configuration and workload variables. Next, the performance variables of the sample can be assessed with respect to the expected normal behavior of the groups to which it belongs, allowing the classification of the test sample as normal or anomalous.

With continuing reference to FIG. 6, the at least one memory 608 can be operatively connected to the at least one processor 610. The at least one memory 608 can store executable instructions and/or computer executable components (e.g., the training component 602, the model 604, the execution component 606, and so on) that, when executed by the at least one processor 610 can facilitate performance of operations. Further, the at least one processor 610 can be utilized to execute computer executable components (e.g., the training component 602, the model 604, the execution component 606, and so on) stored in the at least one memory 608.

For example, the at least one memory 608 can store protocols associated with facilitating detection of anomalies as discussed herein. Further, the at least one memory 608 can facilitate action to control communication between the system 600 and other systems, one or more file storage systems, one or more devices, such that the system 600 employ stored protocols and/or algorithms to achieve improved overall performance of defined entities as described herein.

It should be appreciated that data stores (e.g., memories) components described herein can be either volatile memory or nonvolatile memory, or can include both volatile and nonvolatile memory. By way of example and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of example and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Memory of the disclosed aspects are intended to comprise, without being limited to, these and other suitable types of memory.

The at least one processor 610 can facilitate respective analysis of information related to facilitating detection of anomalies. The at least one processor 610 can be a processor dedicated to analyzing and/or generating information received, a processor that controls one or more components of the system 600, and/or a processor that both analyzes and generates information received and controls one or more components of the system 600.

Figure 7:
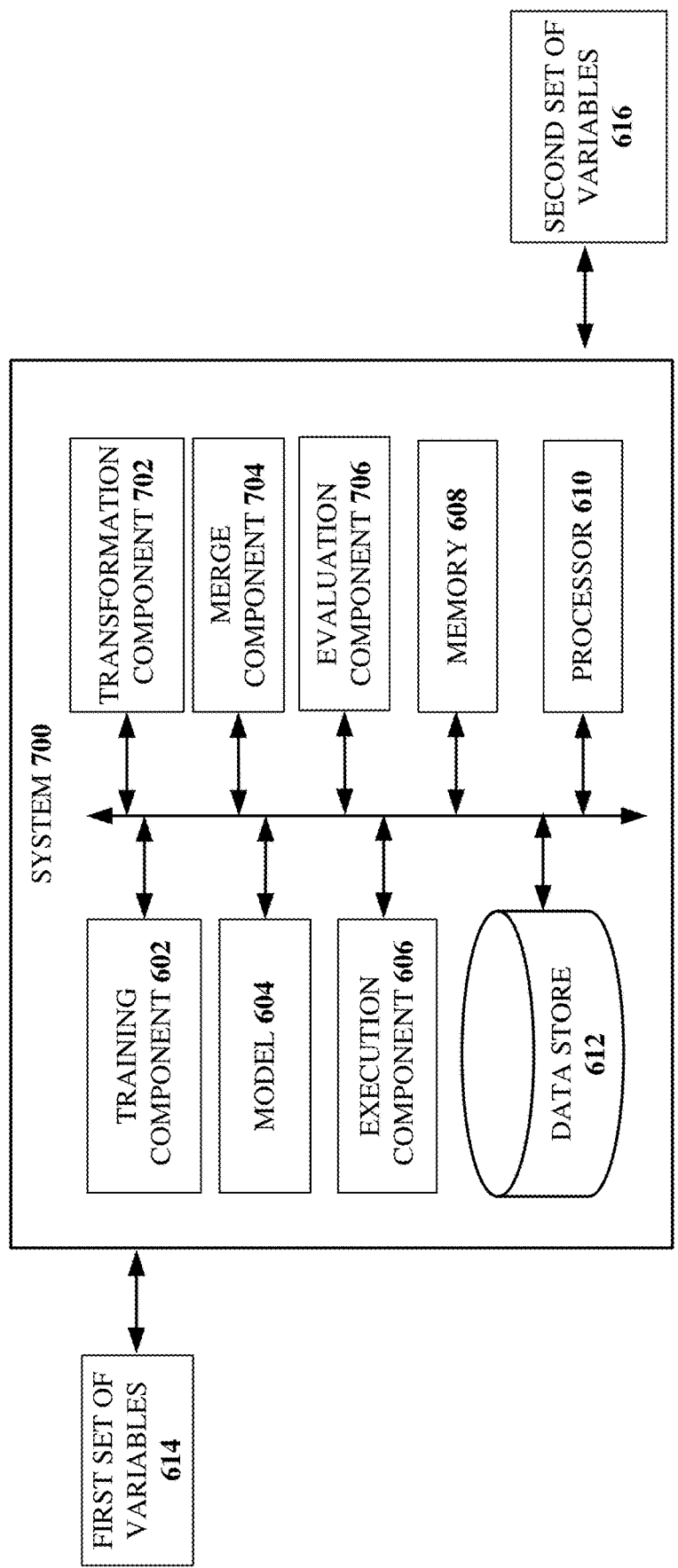
FIG. 7 illustrates an example, non-limiting, system that transforms variables to detect a normal state or an abnormal state of a defined entity in accordance with one or more embodiments described herein.

FIG. 7 illustrates an example, non-limiting, system 700 that transforms variables to detect a normal state or an abnormal state of a defined entity in accordance with one or more embodiments described herein. Repetitive description of like elements employed in other embodiments described herein is omitted for sake of brevity. The system 700 can comprise one or more of the components and/or functionality of the system 600 and vice versa.

The system 700 includes a transformation component 702 that can transform the second set of variables into a representation that comprises the first set of variables. According to some implementations, to transform the second set of variables, the transformation component 702 can constrain the first set of variables based on a derivative representation of the second set of variables.

In another example, to transform the second set of variables, a merge component 704 can group elements of the defined entity based on a similarity function. Further to this example, the merge component 704 can combine variables of different natures of the second set of variables into a single weighted similarity function, resulting in a pairwise similarity. The similarity function can be based on the pairwise similarity between the elements of the defined entity. Further, variables of different natures can comprise configuration variables of the elements of the defined entity and conditions of usage variables of the elements of the defined entity.

Further, an evaluation component 706 can perform anomaly detection of the defined entity based on the first set of variables. For example, the first set of variables can provide context for a definition of normality and a detection of anomalies associated with the defined entity According to some implementations, the evaluation component 706 can evaluate performance variables associated with normal behavior of the defined entity to a group to which the second set of variables belong. Further, a test sample can be classified as normal or anomalous based on result of the evaluation by the evaluation component 706.

Figure 8:
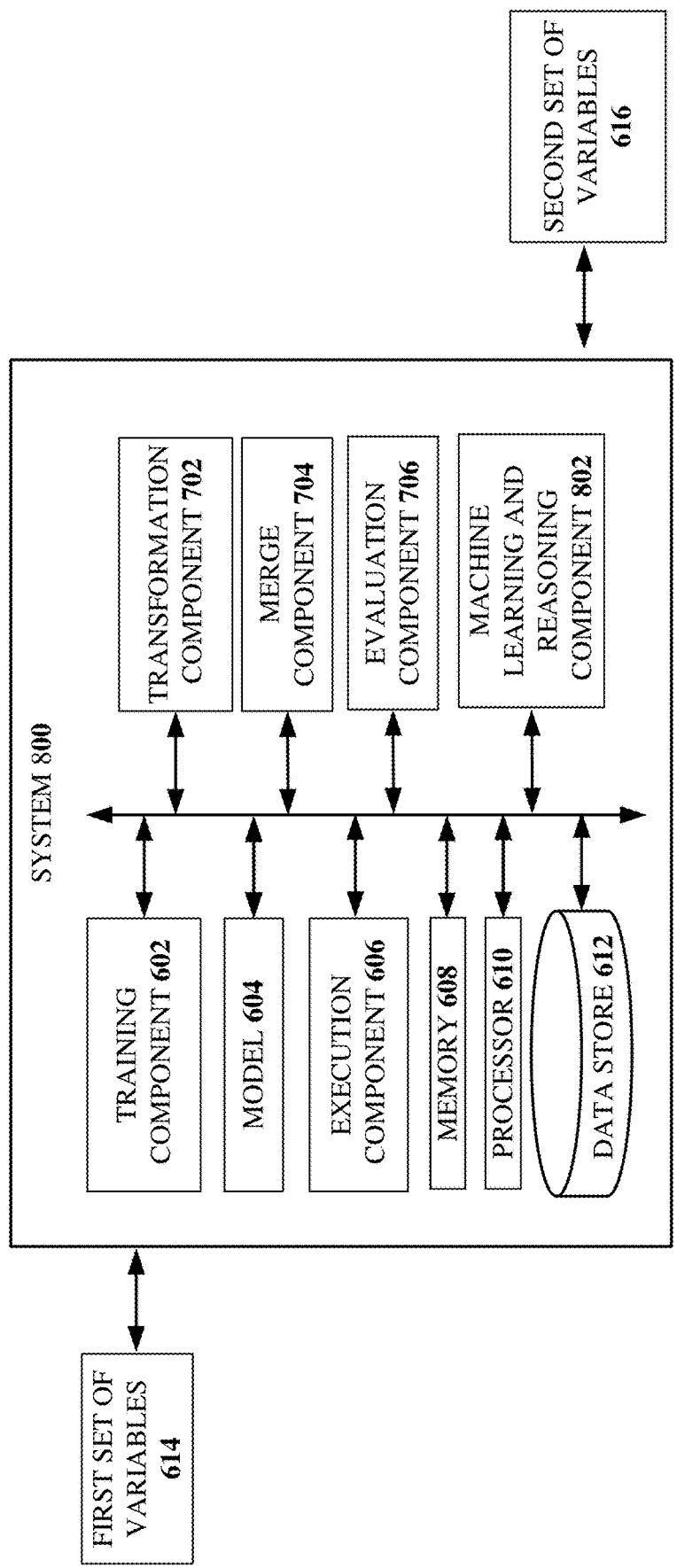
FIG. 8 illustrates an example, non-limiting, system that employs automated learning to facilitate one or more of the disclosed aspects in accordance with one or more embodiments described herein.

FIG. 8 illustrates an example, non-limiting, system 800 that employs automated learning to facilitate one or more of the disclosed aspects in accordance with one or more embodiments described herein. Repetitive description of like elements employed in other embodiments described herein is omitted for sake of brevity. The system 800 can comprise one or more of the components and/or functionality of the system 600, the system 700, and vice versa.

As illustrated, the system 800 can comprise a machine learning and reasoning component 802 that can be utilized to automate one or more of the disclosed aspects. The machine learning and reasoning component 802 can employ automated learning and reasoning procedures (e.g., the use of explicitly and/or implicitly trained statistical classifiers) in connection with performing inference and/or probabilistic determinations and/or statistical-based determinations in accordance with one or more aspects described herein.

For example, the machine learning and reasoning component 802 can employ principles of probabilistic and decision theoretic inference. Additionally, or alternatively, the machine learning and reasoning component 802 can rely on predictive models constructed using machine learning and/or automated learning procedures. Logic-centric inference can also be employed separately or in conjunction with probabilistic methods.

The machine learning and reasoning component 802 can infer which predictor variables (e.g., a first set of variables)

should be evaluated to create target variables (e.g., a second set of variables), which behavior represents normal behavior or anomalous by obtaining knowledge about one or more parameters associated with the defined entity. Based on this knowledge, the machine learning and reasoning component 802 can make an inference based on which behavior is abnormal and should be analyzed further.

As used herein, the term "inference" refers generally to the process of reasoning about or inferring states of a storage system, a component, a module, an environment, and/or devices from a set of observations as captured through events, reports, data and/or through other forms of communication. Inference can be employed to identify if any outliers exist and whether outlier detection should be dynamically performed, for example. The inference can be probabilistic. For example, computation of a probability distribution over states of interest based on a consideration of data and/or events can be performed. The inference can also refer to techniques employed for composing higher-level events from a set of events and/or data. Such inference can result in the construction of new events and/or actions from a set of observed events and/or stored event data, whether or not the events are correlated in close temporal proximity, and whether the events and/or data come from one or several events and/or data sources. Various classification schemes and/or systems (e.g., support vector machines, neural networks, logic-centric production systems, Bayesian belief networks, fuzzy logic, data fusion engines, and so on) can be employed in connection with performing automatic and/or inferred action in connection with the disclosed aspects.

The various aspects (e.g., in connection with detection of anomalies of a defined entity) can employ various artificial intelligence-based protocols for carrying out various aspects thereof. For example, a process for determining if one or more variables predict a normal state of the defined entity or if one or more variables predict an abnormal state of the defined entity can be enabled through an automatic classifier system and process.

A classifier is a function that maps an input attribute vector, x=(x1, x2, x3, x4, xn), to a confidence that the input belongs to a class. In other words, f(x)=confidence(class). Such classification can employ a probabilistic and/or statistical-based analysis (e.g., factoring into the analysis utilities and costs) to provide a prognosis and/or infer one or more actions that should be employed to determine when and how outlier files and/or folders should be evaluated and action taken based on the determination. A Support Vector Machine (SVM) is an example of a classifier that can be employed. The SVM operates by finding a hypersurface in the space of possible inputs, which hypersurface attempts to split the triggering criteria from the non-triggering events. Intuitively, this makes the classification correct for testing data that can be similar, but not necessarily identical to training data. Other directed and undirected model classification approaches (e.g., naïve Bayes, Bayesian networks, decision trees, neural networks, fuzzy logic models, and probabilistic classification models) providing different patterns of independence can be employed. Classification as used herein, can be inclusive of statistical regression that is utilized to develop models of priority.

One or more aspects can employ classifiers that are explicitly trained (e.g., through a generic training data) as well as classifiers that are implicitly trained (e.g., by observing entity behavior, by receiving intrinsic information, by receiving extrinsic information, and so on). For example, SVMs can be configured through a learning or training phase within a classifier constructor and feature selection module. Thus, a classifier(s) can be used to automatically learn and perform a number of functions, including but not limited to determining, according to a predetermined criterion, when to evaluate a parameter further, how to identify the parameters that predict normal behavior, how to identify the parameters that predict abnormal behavior, what to do when an abnormal state is discovered, and so forth.

Additionally, or alternatively, an implementation scheme (e.g., a rule, a policy, and so on) can be applied to control and/or regulate when to (or when not to) detect an anomalous state. In some implementations, based upon a predefined criterion, the rules-based implementation can automatically attempt to detect the anomalous state. In response thereto, the rule-based implementation can automatically interpret and carry out functions associated with the anomalous state detection by employing predefined rule(s) and/or programmed rule(s) based upon any desired criteria.

Methods that can be implemented in accordance with the disclosed subject matter, will be better appreciated with reference to the following flow charts. While, for purposes of simplicity of explanation, the methods are shown and described as a series of blocks, it is to be understood and appreciated that the disclosed aspects are not limited by the number or order of blocks, as some blocks can occur in different orders and/or at substantially the same time with other blocks from what is depicted and described herein. Moreover, not all illustrated blocks can be required to implement the disclosed methods. It is to be appreciated that the functionality associated with the blocks can be implemented by software, hardware, a combination thereof, or any other suitable means (e.g., device, system, process, component, and so forth). Additionally, it should be further appreciated that the disclosed methods are capable of being stored on an article of manufacture to facilitate transporting and transferring such methods to various devices. Those skilled in the art will understand and appreciate that the methods could alternatively be represented as a series of interrelated states or events, such as in a state diagram.

Figure 9:
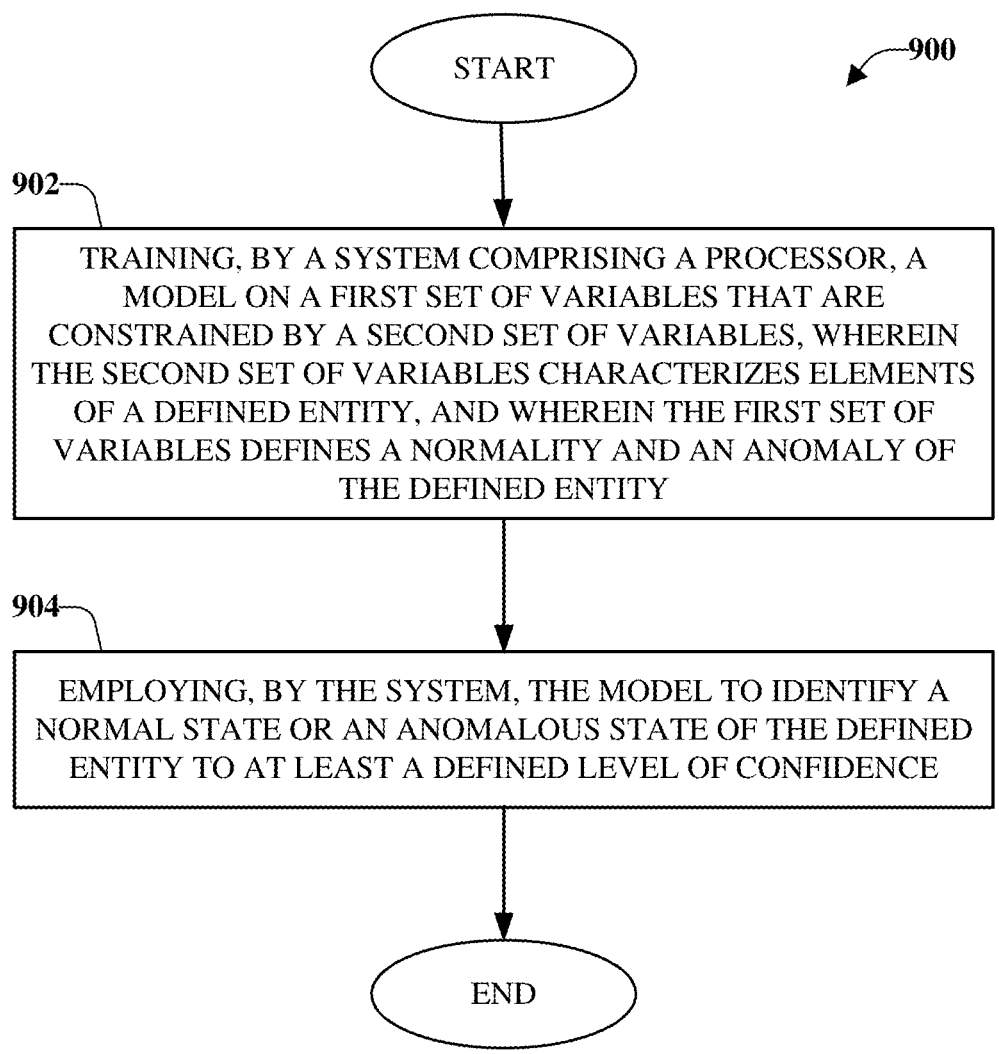
FIG. 9 illustrates a flow diagram of an example, non-limiting, computer-implemented method that facilitates detection of anomalies in accordance with one or more embodiments described herein.

FIG. 9 illustrates a flow diagram of an example, non-limiting, computer-implemented method 900 that facilitates detection of anomalies in accordance with one or more embodiments described herein. Repetitive description of like elements employed in other embodiments described herein is omitted for sake of brevity.

In some implementations, a system comprising a processor can perform the computer-implemented method 900 and/or other methods discussed herein. In other implementations, a device comprising a processor can perform the computer-implemented method 900 and/or other methods discussed herein. For example, the device can be a node device in other implementations, a machine-readable storage medium, can comprise executable instructions that, when executed by a processor, facilitate performance of operations, which can be the operations discussed with respect to the computer-implemented method 900 and/or other methods discussed herein. In further implementations, a computer readable storage device comprising executable instructions that, in response to execution, cause a system comprising a processor to perform operations, which can be operations discussed with respect to the computer-implemented method 900 and/or other methods discussed herein.

At 902 of the computer-implemented method 900, a device comprising a processor can train a model on a first set of variables that are constrained by a second set of variables (e.g., via the training component 602). The second set of variables can characterize elements of a defined entity.

Further, the first set of variables can define a normality and an anomaly of the defined entity.

Further, at 904, the device can employ the model to identify a normal state or an anomalous state of the defined entity to at least a defined level of confidence (e.g., via the execution component 606). For example, the defined level of confidence can be a level determined to be acceptable and can represent a percentage of accurate determinations.

Figure 10:
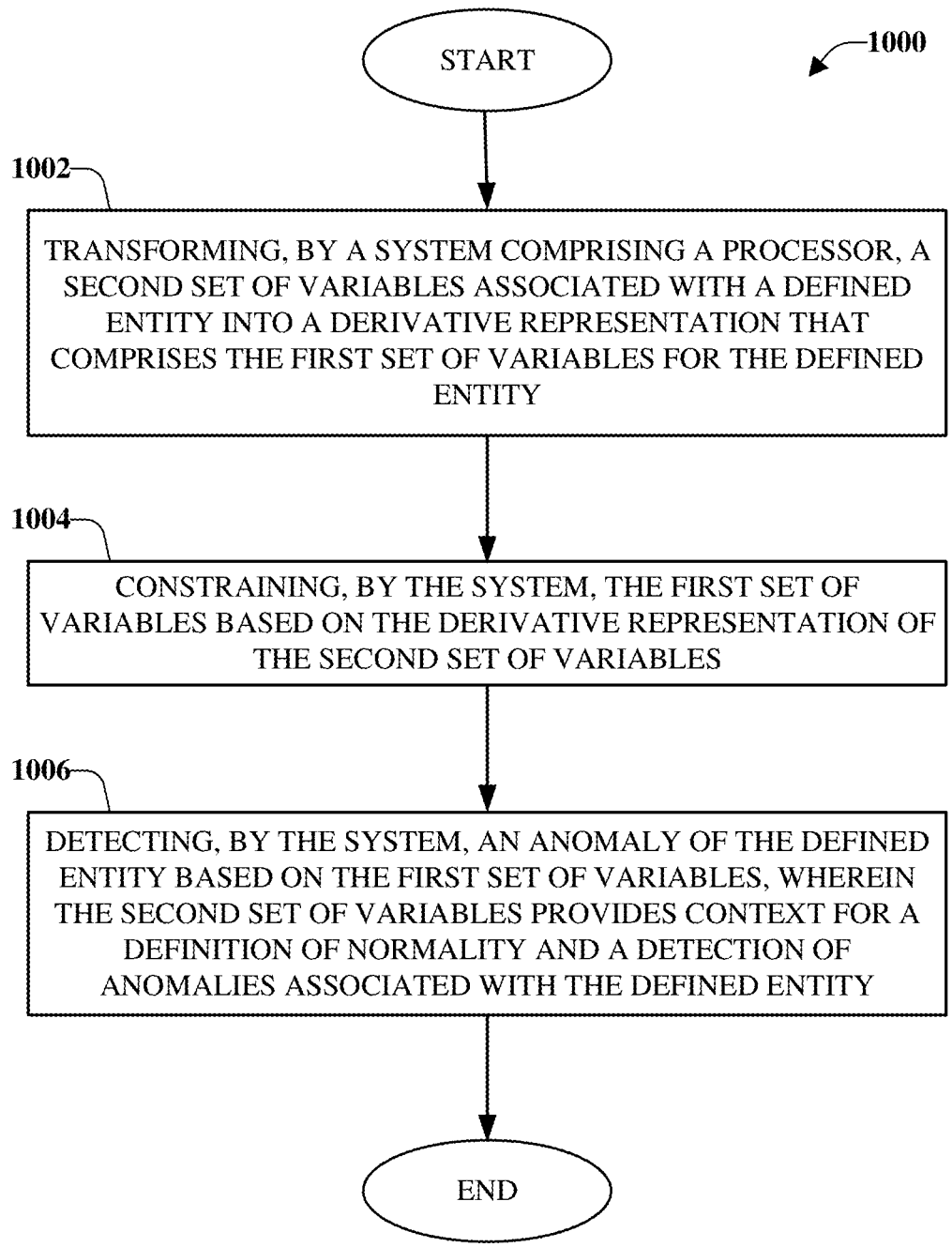
FIG. 10 illustrates a flow diagram of an example, non-limiting, computer-implemented method that detest an anomaly of a defined entity based on a transformation of sets of variables in accordance with one or more embodiments described herein.

FIG. 10 illustrates a flow diagram of an example, non-limiting, computer-implemented method 1000 that detect an anomaly of a defined entity based on a transformation of sets of variables in accordance with one or more embodiments described herein. Repetitive description of like elements employed in other embodiments described herein is omitted for sake of brevity.

In some implementations, a system comprising a processor can perform the computer-implemented method 1000 and/or other methods discussed herein. In other implementations, a device comprising a processor can perform the computer-implemented method 1000 and/or other methods discussed herein. For example, the device can be a node device in other implementations, a machine-readable storage medium, can comprise executable instructions that, when executed by a processor, facilitate performance of operations, which can be the operations discussed with respect to the computer-implemented method 1000 and/or other methods discussed herein. In further implementations, a computer readable storage device comprising executable instructions that, in response to execution, cause a system comprising a processor to perform operations, which can be operations discussed with respect to the computer-implemented method 1000 and/or other methods discussed herein.

At 1002 of the computer-implemented method 1000, a device comprising a processor can transform a second set of variables associated with a defined entity into a derivative representation that comprises a first set of variables for the defined entity (e.g., via the transformation component 702). Further, at 1004, the first set of variables can be constrained based on the derivative representation of the second set of variables (e.g., via the transformation component 702).

In addition, at 1006 of the computer-implemented method 1000, the device can detect an anomaly of the defined entity based on the first set of variables (e.g., via the evaluation component 706). The second set of variables can provide context for a definition of normality and a detection of anomalies associated with the defined entity. According to various implementations, a model can be trained on the first set of variables that are constrained by the second set of variables. Upon or after training of the model, the model can be employed to identify a normal state or an anomalous state of the defined entity to a defined level of confidence.

Figure 11:
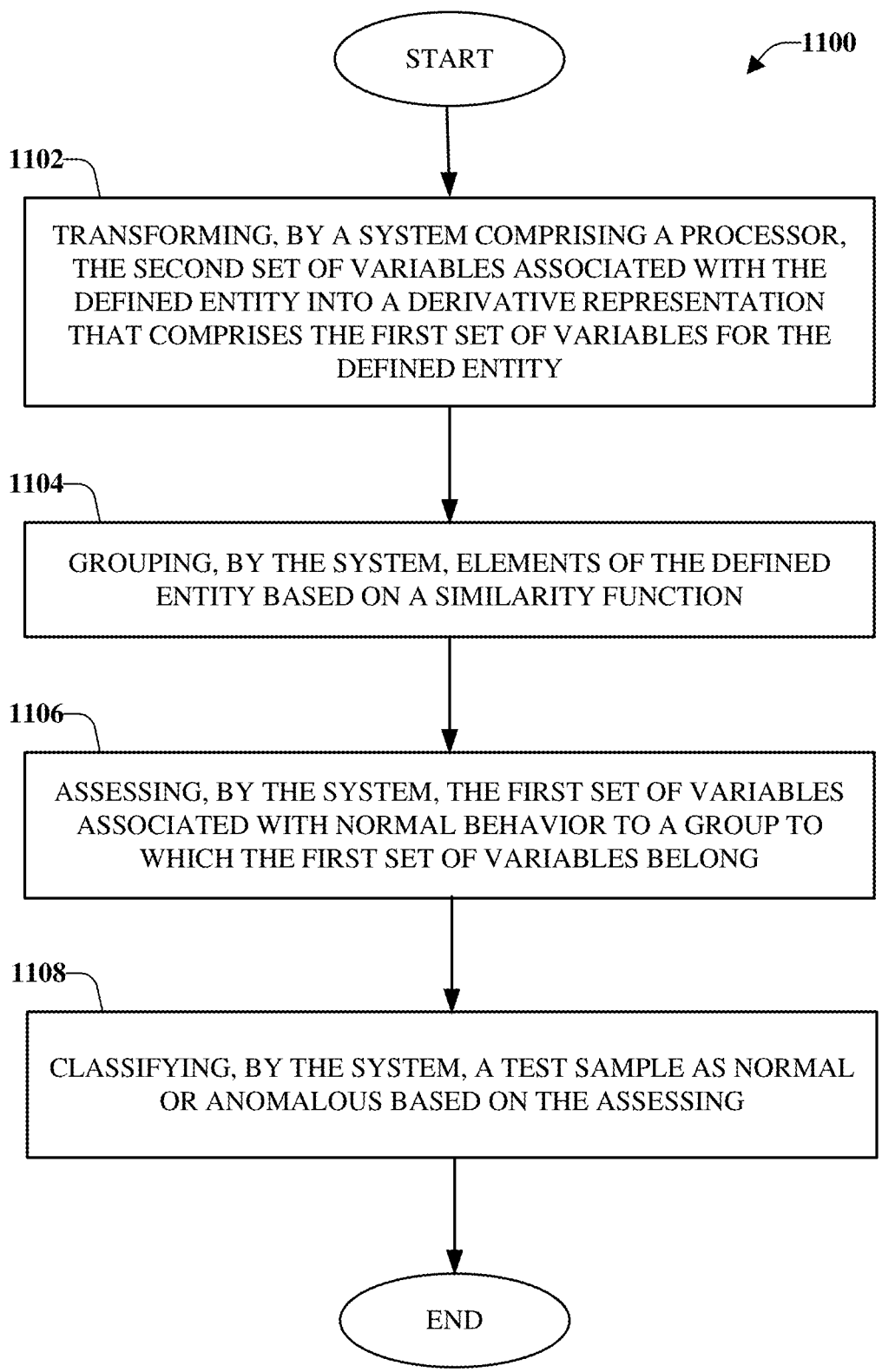
FIG. 11 illustrates a flow diagram of an example, non-limiting, computer-implemented method that transforms variables associated with a defined entity into a derivative representation to detect anomalies in accordance with one or more embodiments described herein.

FIG. 11 illustrates a flow diagram of an example, non-limiting, computer-implemented method 1100 that transforms variables associated with a defined entity into a derivative representation to detect anomalies in accordance with one or more embodiments described herein. Repetitive description of like elements employed in other embodiments described herein is omitted for sake of brevity.

In some implementations, a system comprising a processor can perform the computer-implemented method 1100 and/or other methods discussed herein. In other implementations, a device comprising a processor can perform the computer-implemented method 1100 and/or other methods discussed herein. For example, the device can be a node device in other implementations, a machine-readable storage medium, can comprise executable instructions that, when executed by a processor, facilitate performance of operations, which can be the operations discussed with respect to the computer-implemented method 1100 and/or other methods discussed herein. In further implementations, a computer readable storage device comprising executable instructions that, in response to execution, cause a system comprising a processor to perform operations, which can be operations discussed with respect to the computer-implemented method 1100 and/or other methods discussed herein.

At 1102 of the computer-implemented method 1100, a device comprising a processor can transform a second set of variables associated with a defined entity into a derivative representation that comprises the first set of variables for the defined entity (e.g., via the transformation component 702). As indicated at 1104, the transformation can comprise grouping elements of the defined entity based on a similarity function (e.g., via the transformation component 702). The similarity function can be based on a pairwise similarity between the elements of the defined entity. Further, the pairwise similarity can be based on combining, by the device, variables of different natures of the second set of variables into a single weighted similarity function. Variables of different natures can comprise configuration variables of the elements of the defined entity and conditions of usage variables of the elements of the defined entity.

The computer-implemented method 1100 can also include, at 1106, accessing by the device the first set of variables associated with normal behavior to a group to which the first set of variables belong (e.g., via the evaluation component 706). Further, at 1108, the device can classify a test sample as normal or anomalous based on the assessment (e.g., via the evaluation component 706). The first set of variables can comprise performance variables.

To validate the disclosed aspects related to the extra-exogenous method for anomaly detection, various experiments were performed. Specifically, an anomaly detection model that employs the ideas of variable categorization and group formation described herein was trained. For this, three months of real telemetry data from 238 storage platform clusters were used. Of this set, 213 clusters were labelled, and 25 had some type of anomaly. The objective was to train a machine-learning model that can classify test samples as normal or anomalous based on telemetry. The data contained the variables illustrated in Table 1 below.

TABLE 1

| Configuration | Workload | Performance |
| --- | --- | --- |
| cluster.node.count.all | cluster.net.ext.bytes.in.rate | cluster.cpu.sys.avg |
| cluster.cpu.count | cluster.net.ext.bytes.out.rate | cluster.cpu.user.avg |
| | ifs.ops.in.rate | cluster.protostats.smb2.time__avg |
| | ifs.ops.out.rate | |
| | cluster.protostats.smb2.in__rate | |
| | cluster.protostats.smb2.out__rate | |

As described above, the variables were separated into different categories comprising configuration, workload, and performance categories. As indicated in Table 1, domain knowledge was used.

Next, 188 normal clusters were randomly separated to train the model of normality and define the expected normal ranges of the performance variables. Before training the model, the data was normalized.

Initially, a clustering algorithm was employed for the grouping portion. In this experiment, hierarchical clustering, parameterized with 25 clusters, was utilized. To compute the pairwise similarity between elements from the dataset (as employed by the clustering algorithm), a proposed distance measure with $\alpha=0.5$ was used. This distance measurement provides equal weight to configuration and workload variables. For the underlying configuration component of the distance measure, the sum of absolute difference between terms was employed. For the workload component, the variables were represented as distributions and the distances were computed based on Jensen-Shannon divergence between the variables.

Next, the centroid of each group was computed with respect to the performance variables. Normality was defined based on the distance from each element of a group to the group's centroid, considering only the performance variables. By doing this with the normal clusters of the training set, acceptable range of distances for each performance variable can be defined. In this set of experiments, the acceptable range of distances was defined as the interval $N=[q1-1.5*IQR, q3+1.5*IQR]$, where $\{q1,q3\}$ are the first and third quartiles of all the distances within the group and IQR is the inter-quartile range. To compute the distances to the centroid, the same similarity function, with $\alpha=0.5$, was employed.

Figure 12:
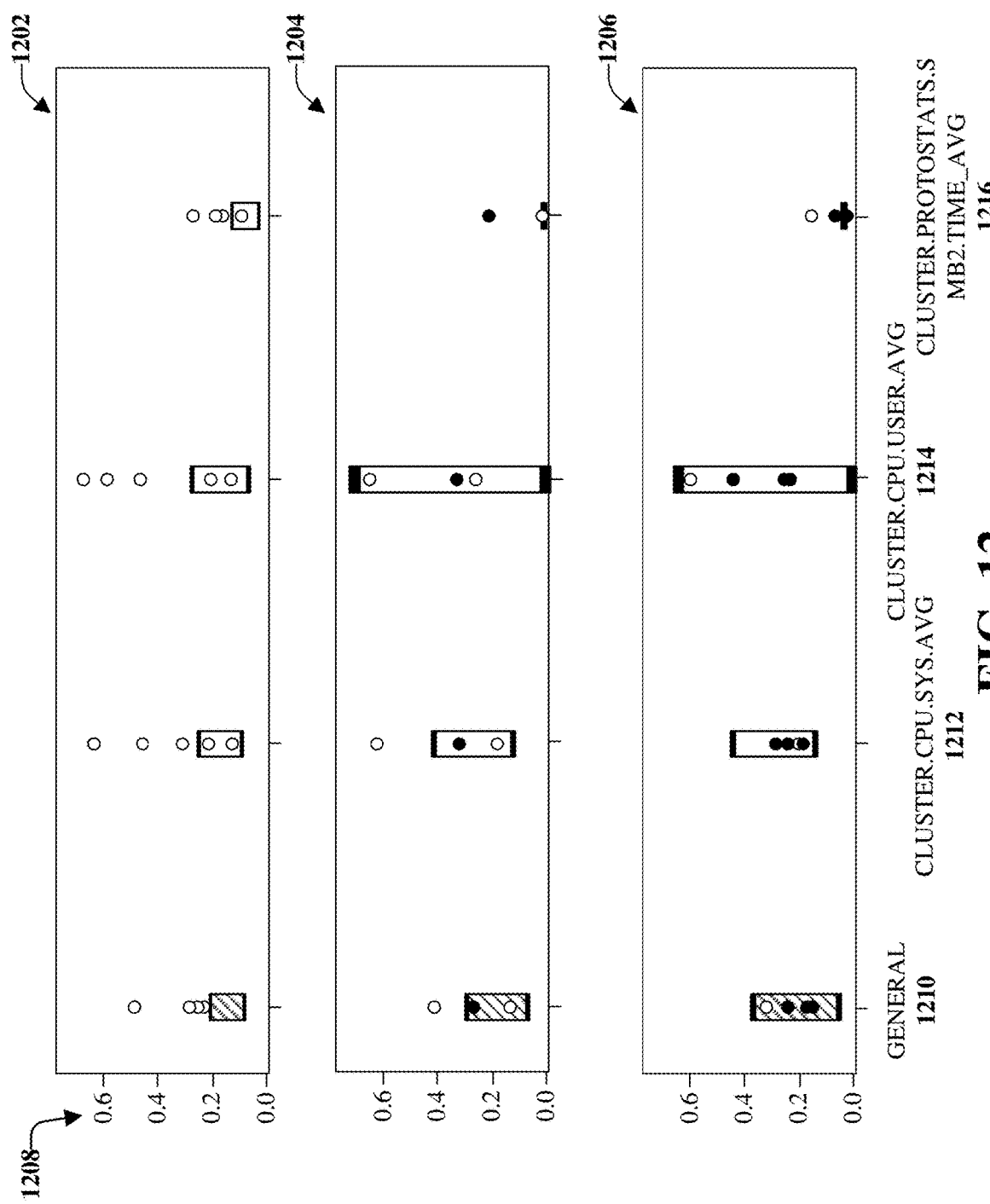
FIG. 12 illustrates, for some groups, the obtained normal ranges of distances to the centroid for a subset of the performance variables.

FIG. 12 illustrates, for some groups, the obtained normal ranges of distances to the centroid for a subset of the performance variables. FIG. 12 also illustrates the normal ranges for the combination of the performance variables (referred to as "general"). In this set of experiments, the combination within a group was defined as the mean of all the per-performance-variable distance to the centroid.

In further detail, FIG. 12 illustrates an example model of normality from a set of 188 normal clusters, and associated anomaly detection results. The first group of boxplots represents performance variables for a first cluster group 1202; the second group of boxplots represents performance variables for a second cluster group 1204; and the third group of boxplots represents performance variables for a third cluster group 1206. Distance to centroid 1208 is represented on the vertical axis. The first boxplot in each group is a general boxplot 1210, the second boxplot in each group is for cluster.cpu.sys.avg 1212, the third boxplot in each group is for a cluster.cpu.user.avg 1214, and the fourth boxplot in each group is for a cluster.protostats.smb2.time_avg 1216. The unshaded boxplots represent a normal range (measurement) and the shaded boxplots represent a normal range (general). Further, the unshaded circles represent test cases (dudl) and the shaded circles represent test cases (normal).

More specifically, the unshaded bars indicate the expected normal ranges of each performance variable of each cluster group. The normal range is defined via per-variable the inter-quartile range of distances to the centroid of the group. The shaded bars indicate the expected "general" normal ranges, defined via the inter-quartile range of the mean of all per-variable distances to the centroid of the group.

After training the model to learn the normal ranges, unseen samples were able to be classified as normal or anomalous. To do this, a validation set was built with the telemetry of the remaining 25 normal storage platform clusters of the original set, which were not used in the training phase, and of the 25 anomalous clusters. An evaluation was performed to determine if the model could correctly classify normal test cases as normal and anomalous test cases as anomalous.

To begin, analysis was performed to identify to which group each test case belonged using configuration and workload variables. In this set of experiments, a test case was assigned to the nearest group, by computing the minimal distance from the test case to the groups' centroids. Such distance was computed using the similarity function described above, with $\alpha=0.5$.

In this set of experiments, the centroid of each group was computed with respect to the performance variables alone. As illustrated in FIG. 12, the expected normal range of each performance variable was defined via the IQR of all distances to the groups' centroid. From there the distance from the test case to the group's centroid can also be computed, with respect to the performance variables, and verification can be made whether such distance was within the expected normal ranges. If the distance fell outside the normal range, the test case was classified as anomalous. Otherwise, it was classified as normal.

In FIG. 12, examples of classification for different test cases are provided, which are represented by the shaded and unshaded circles. A shaded dot indicates that the test case is known to be normal, and an unshaded dot indicates that the test case is known to be anomalous. To visually assess the quality of the classification, the largest possible number of unshaded dots outside the normal ranges should be depicted, considering both the general and per-variable ranges. Conversely, the largest possible number of shaded dots within the normal ranges should be depicted.

It is noted, however, that, in some cases, a performance variable might indicate that the test case is normal, but the general evaluation indicates otherwise. This was the case for variable cluster.cpu.user.avg in all test cases assigned to group 1. Note also that at least one of them was correctly classified as anomalous (unshaded circle outside the general range). This happened because the same test case was far away from the normal range of the variable cluster.cpu.sys.avg, which eventually "pulled" the entire cluster outside the expected general normal range. This analysis shows that a method as discussed herein can leverage the variable categorization to not only classify test cases as normal or anomalous, but also to understand which performance variables have the strongest influence on the classification.

Figure 13:
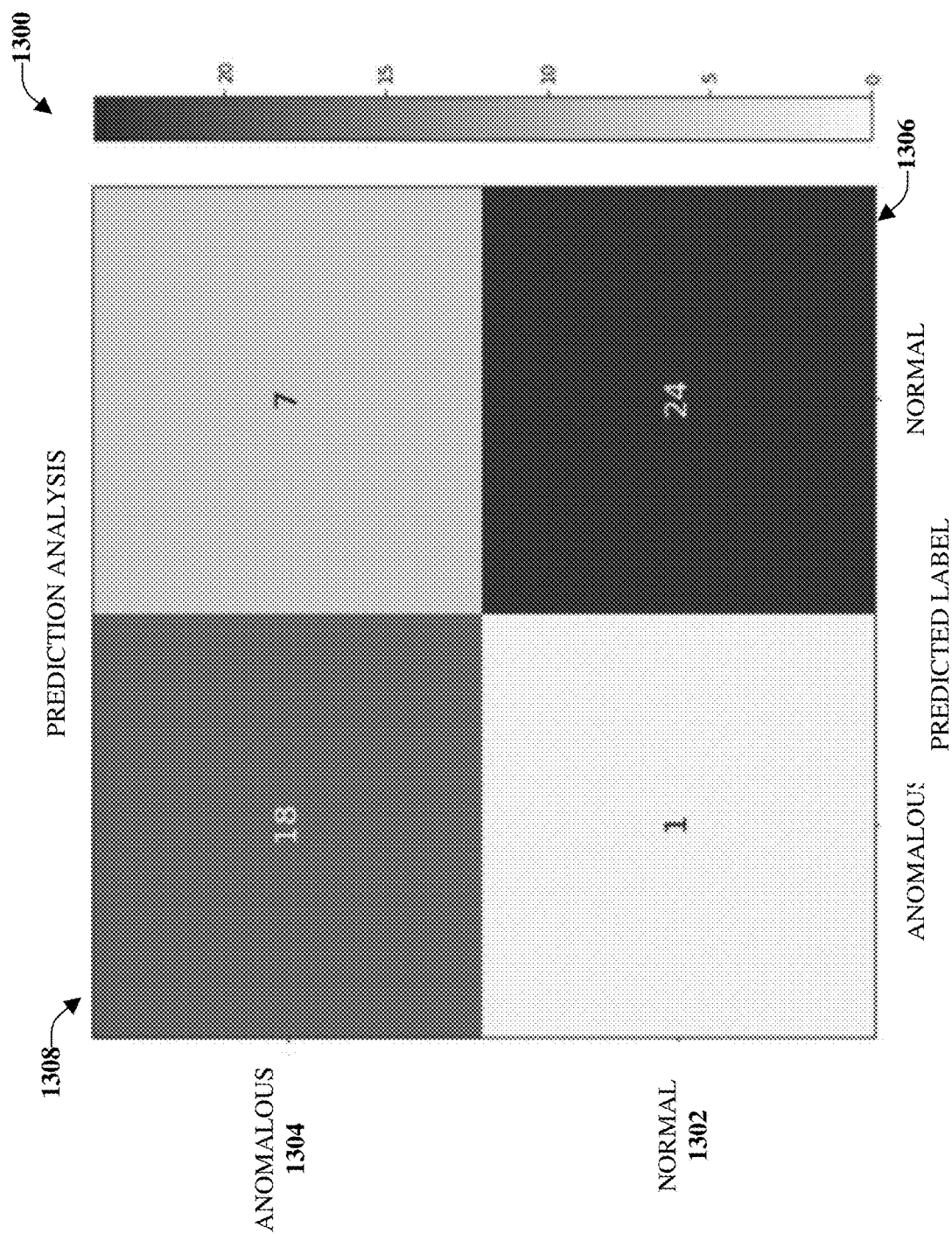
FIG. 13 illustrates a confusion matrix for the classification of test cases.

FIG. 13 and Table 2 below illustrate the quality of the classification results for the 50 test cases used in the model validation set. More specifically, FIG. 13 illustrates a confusion matrix 1300 for the classification of 50 test cases. Further, Table 2 illustrates classification metrics derived from the confusion matrix of FIG. 13.

TABLE 2

| Measure | Value |
| --- | --- |
| Precision Anomalous | 0.95 |
| Recall Anomalous | 0.72 |
| F1-score Anomalous | 0.82 |
| Precision Normal | 0.77 |
| Recall Normal | 0.96 |
| F1-score Normal | 0.86 |
| Overall accuracy | 0.84 |
| P-value | $8 \times 10^{-7}$ |

The set consisted of the remaining 25 normal clusters 1302 (separated from the training set) and of the 25 clusters containing some type of anomaly (anomalous 1304). As illustrated, the model trained as descried herein did a remarkable job in the detection of normal clusters. Out of the 25 normal clusters, 24 were classified as normal (indicated at 1306), a recall of 96%. The recall of the anomalous class, on the other hand, dropped to 72%, since 18 out of the 25 anomalous clusters (indicated at 1308) were correctly classified. This shows a certain tendency of the model to yield false-anomalous labels.

Nonetheless, the precision of 95% (e.g., a good defined level of confidence) achieved for the anomalous class is a clear indication that the proposed extra-exogenous model can capture variations in the telemetry that correlate with anomalous behaviors. This is further evidenced by the relatively F1-scores of both the normal and anomalous classes. Finally, an overall accuracy of 84% reassures the potential of the disclosed aspects.

In any case, the disclosed aspects provide for the separation of telemetry variables into categories and the leverage of such separation to develop an extra-exogenous approach to solve the anomaly detection. Such approach provides a sense of context where normal and anomalous behaviors appear more naturally. In practice, such context is derived from the grouping step using configuration and workload variables, which is then used to constrain the expected normal ranges of the performance variables. By doing this, focus can be placed on the right variables and decisions can be made more confidently based on the analysis of the classification results. Even though clustering is employed, algorithms and distance to centroids with relative success, the disclosed aspects are agnostic about the actual algorithms used in the model.

As used herein, the term "storage device," "first storage device," "storage cluster nodes," "storage system," and the like, can include, for example, private or public cloud computing systems for storing data as well as systems for storing data comprising virtual infrastructure and those not comprising virtual infrastructure. The term "I/O request" (or simply "I/O") can refer to a request to read and/or write data.

The term "cloud" as used herein can refer to a cluster of nodes (e.g., set of network servers), for example, within a distributed object storage system, that are communicatively and/or operatively coupled to one another, and that host a set of applications utilized for servicing user requests. In general, the cloud computing resources can communicate with user devices via most any wired and/or wireless communication network to provide access to services that are based in the cloud and not stored locally (e.g., on the user device). A typical cloud-computing environment can include multiple layers, aggregated together, that interact with one another to provide resources for end-users.

Further, the term "storage device" can refer to any Non-Volatile Memory (NVM) device, including Hard Disk Drives (HDDs), flash devices (e.g., NAND flash devices), and next generation NVM devices, any of which can be accessed locally and/or remotely (e.g., via a Storage Attached Network (SAN)). In some embodiments, the term "storage device" can also refer to a storage array comprising one or more storage devices. In various embodiments, the term "object" refers to an arbitrary-sized collection of user data that can be stored across one or more storage devices and accessed using I/O requests.

Further, a storage cluster can include one or more storage devices. For example, a distributed storage system can include one or more clients in communication with a storage cluster via a network. The network can include various types of communication networks or combinations thereof including, but not limited to, networks using protocols such as Ethernet, Internet Small Computer System Interface (iSCSI), Fibre Channel (FC), and/or wireless protocols. The clients can include user applications, application servers, data management tools, and/or testing systems.

As utilized herein an "entity," "client," "user," and/or "application" can refer to any system or person that can send I/O requests to a storage system. For example, an entity, can be one or more computers, the Internet, one or more systems, one or more commercial enterprises, one or more computers, one or more computer programs, one or more machines, machinery, one or more actors, one or more users, one or more customers, one or more humans, and so forth, hereinafter referred to as an entity or entities depending on the context.

Figure 14:
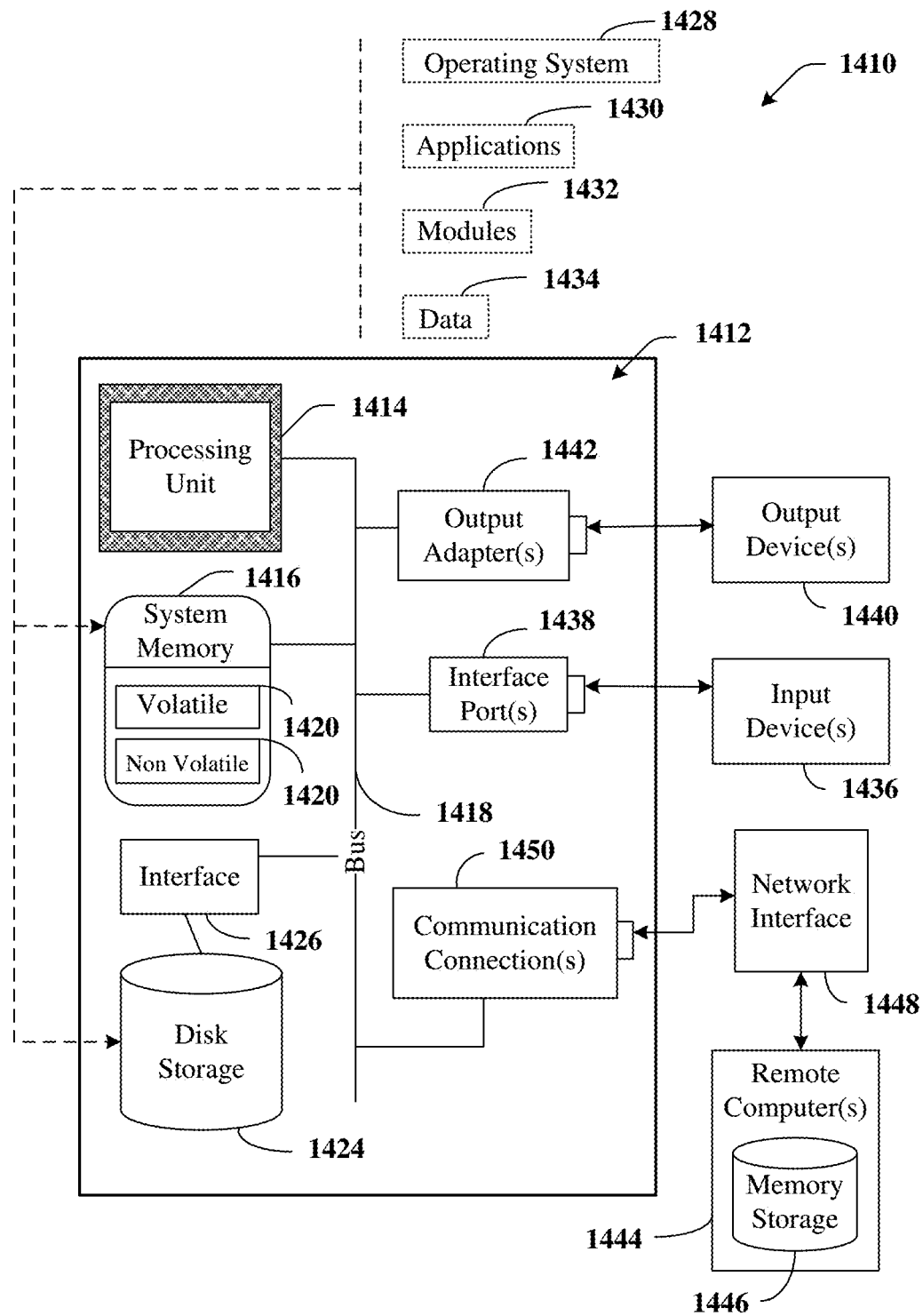
FIG. 14 illustrates an example, non-limiting, computing environment in which one or more embodiments described herein can be facilitated.

In order to provide a context for the various aspects of the disclosed subject matter, FIG. 14 as well as the following discussion are intended to provide a brief, general description of a suitable environment in which the various aspects of the disclosed subject matter can be implemented.

With reference to FIG. 14, an example environment 1410 for implementing various aspects of the aforementioned subject matter comprises a computer 1412. The computer 1412 comprises a processing unit 1414, a system memory 1416, and a system bus 1418. The system bus 1418 couples system components including, but not limited to, the system memory 1416 to the processing unit 1414. The processing unit 1414 can be any of various available processors. Multi-core microprocessors and other multiprocessor architectures also can be employed as the processing unit 1414.

The system bus 1418 can be any of several types of bus structure(s) including the memory bus or memory controller, a peripheral bus or external bus, and/or a local bus using any variety of available bus architectures including, but not limited to, 8-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The system memory 1416 comprises volatile memory 1420 and nonvolatile memory 1422. The basic input/output system (BIOS), containing the basic routines to transfer information between elements within the computer 1412, such as during start-up, is stored in nonvolatile memory 1422. By way of illustration, and not limitation, nonvolatile memory 1422 can comprise read only memory (ROM), programmable ROM (PROM), electrically programmable ROM (EPROM), electrically erasable PROM (EEPROM), or flash memory. Volatile memory 1420 comprises random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

Computer 1412 also comprises removable/non-removable, volatile/non-volatile computer storage media. FIG. 14 illustrates, for example a disk storage 1424. Disk storage 1424 comprises, but is not limited to, devices like a magnetic disk drive, floppy disk drive, tape drive, Jaz drive, Zip drive, LS-100 drive, flash memory card, or memory stick. In addition, disk storage 1424 can comprise storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1424 to the system bus 1418, a removable or non-removable interface is typically used such as interface 1426.

It is to be appreciated that FIG. 14 describes software that acts as an intermediary between users and the basic computer resources described in suitable operating environment 1410. Such software comprises an operating system 1428. Operating system 1428, which can be stored on disk storage 1424, acts to control and allocate resources of the computer 1412. System applications 1430 take advantage of the management of resources by operating system 1428 through program modules 1432 and program data 1434 stored either in system memory 1416 or on disk storage 1424. It is to be appreciated that one or more embodiments of the subject disclosure can be implemented with various operating systems or combinations of operating systems.

A user enters commands or information into the computer 1412 through input device(s) 1436. Input devices 1436 comprise, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1414 through the system bus 1418 via interface port(s) 1438. Interface port(s) 1438 comprise, for example, a serial port, a parallel port, a game port, and a universal serial bus (USB). Output device(s) 1440 use some of the same type of ports as input device(s) 1436. Thus, for example, a USB port can be used to provide input to computer 1412, and to output information from computer 1412 to an output device 1440. Output adapters 1442 are provided to illustrate that there are some output devices 1440 like monitors, speakers, and printers, among other output devices 1440, which require special adapters. The output adapters 1442 comprise, by way of illustration and not limitation, video and sound cards that provide a means of connection between the output device 1440 and the system bus 1418. It should be noted that other devices and/or systems of devices provide both input and output capabilities such as remote computer(s) 1444.

Computer 1412 can operate in a networked environment using logical connections to one or more remote computers, such as remote computer(s) 1444. The remote computer(s) 1444 can be a personal computer, a server, a router, a network PC, a workstation, a microprocessor based appliance, a peer device or other common network node and the like, and typically comprises many or all of the elements described relative to computer 1412. For purposes of brevity, only a memory storage device 1446 is illustrated with remote computer(s) 1444. Remote computer(s) 1444 is logically connected to computer 1412 through a network interface 1448 and then physically connected via communication connection 1450. Network interface 1448 encompasses communication networks such as local-area networks (LAN) and wide-area networks (WAN). LAN technologies comprise Fiber Distributed Data Interface (FDDI), Copper Distributed Data Interface (CDDI), Ethernet/IEEE 802.3, Token Ring/IEEE 802.5 and the like. WAN technologies comprise, but are not limited to, point-to-point links, circuit switching networks like Integrated Services Digital Networks (ISDN) and variations thereon, packet switching networks, and Digital Subscriber Lines (DSL).

Communication connection(s) 1450 refers to the hardware/software employed to connect the network interface 1448 to the system bus 1418. While communication connection 1450 is shown for illustrative clarity inside computer 1412, it can also be external to computer 1412. The hardware/software necessary for connection to the network interface 1448 comprises, for exemplary purposes only, internal and external technologies such as, modems including regular telephone grade modems, cable modems and DSL modems, ISDN adapters, and Ethernet cards.

Figure 15:
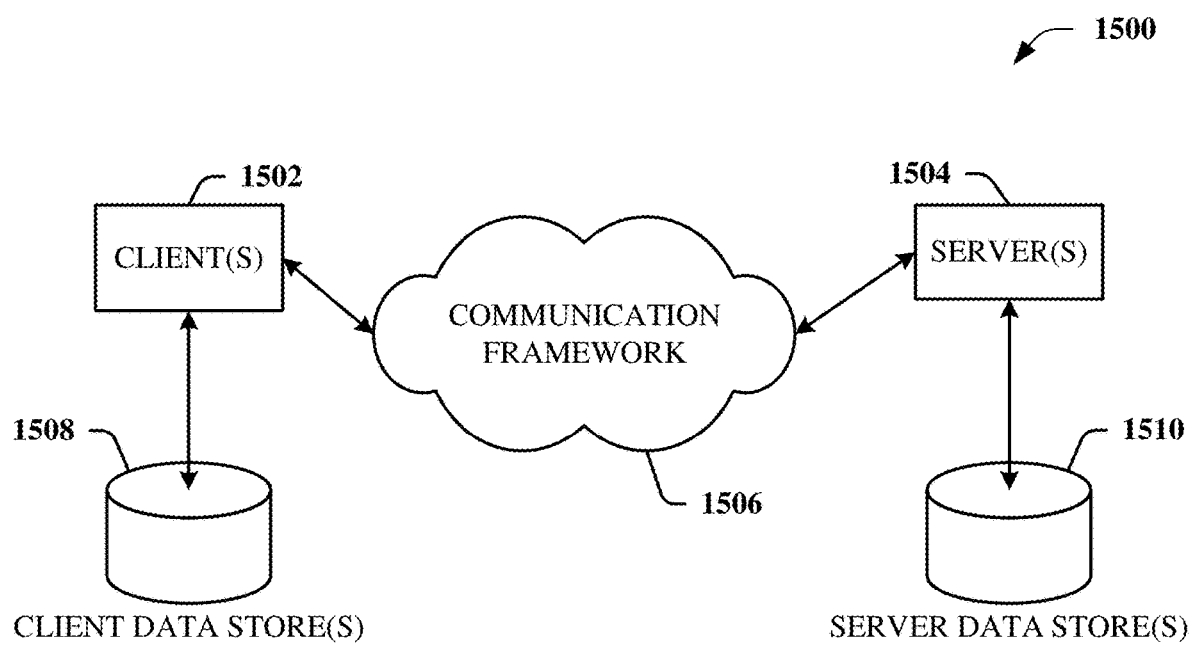
FIG. 15 illustrates an example, non-limiting, networking environment in which one or more embodiments described herein can be facilitated.

FIG. 15 is a schematic block diagram of a sample computing environment 1500 with which the disclosed subject matter can interact. The sample computing environment 1500 includes one or more client(s) 1502. The client(s) 1502 can be hardware and/or software (e.g., threads, processes, computing devices). The sample computing environment 1500 also includes one or more server(s) 1504. The server(s) 1504 can also be hardware and/or software (e.g., threads, processes, computing devices). The servers 1504 can house threads to perform transformations by employing one or more embodiments as described herein, for example. One possible communication between a client 1502 and servers 1504 can be in the form of a data packet adapted to be transmitted between two or more computer processes. The sample computing environment 1500 includes a communication framework 1506 that can be employed to facilitate communications between the client(s) 1502 and the server(s) 1504. The client(s) 1502 are operably connected to one or more client data store(s) 1508 that can be employed to store information local to the client(s) 1502. Similarly, the server(s) 1504 are operably connected to one or more server data store(s) 1510 that can be employed to store information local to the servers 1504.

Reference throughout this specification to "one embodiment," or "an embodiment," means that a particular feature, structure, or characteristic described in connection with the embodiment is included in at least one embodiment. Thus, the appearances of the phrase "in one embodiment," "in one aspect," or "in an embodiment," in various places throughout this specification are not necessarily all referring to the same embodiment. Furthermore, the particular features, structures, or characteristics can be combined in any suitable manner in one or more embodiments.

As used in this disclosure, in some embodiments, the terms "component," "system," "interface," "manager," and the like are intended to refer to, or comprise, a computer-related entity or an entity related to an operational apparatus with one or more specific functionalities, wherein the entity can be either hardware, a combination of hardware and software, software, or software in execution, and/or firmware. As an example, a component can be, but is not limited to being, a process running on a processor, a processor, an object, an executable, a thread of execution, computer-executable instructions, a program, and/or a computer. By way of illustration and not limitation, both an application running on a server and the server can be a component One or more components can reside within a process and/or thread of execution and a component can be localized on one computer and/or distributed between two or more computers. In addition, these components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by one or more processors, wherein the processor can be internal or external to the apparatus and can execute at least a part of the software or firmware application. As yet another example, a component can be an apparatus that provides specific functionality through electronic components without mechanical parts, the electronic components can comprise a processor therein to execute software or firmware that confer(s) at least in part the functionality of the electronic components. In an aspect, a component can emulate an electronic component via a virtual machine, e.g., within a cloud computing system. While various components have been illustrated as separate components, it will be appreciated that multiple components can be implemented as a single component, or a single component can be implemented as multiple components, without departing from example embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Inference can also refer to techniques employed for composing higher-level events from a set of events and/or data. Such inference results in the construction of new events or actions from a set of observed events and/or stored event data, whether the events are correlated in close temporal proximity, and whether the events and data come from one or several event and data sources. Various classification schemes and/or systems (e.g., support vector machines, neural networks, expert systems, Bayesian belief networks, fuzzy logic, and data fusion engines) can be employed in connection with performing automatic and/or inferred action in connection with the disclosed subject matter.

In addition, the various embodiments can be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, machine-readable device, computer-readable carrier, computer-readable media, machine-readable media, computer-readable (or machine-readable) storage/communication media. For example, computer-readable storage media can comprise, but are not limited to, radon access memory (RAM), read only memory (ROM), electrically erasable programmable read only memory (EEPROM), flash memory or other memory technology, solid state drive (SSD) or other solid-state storage technology, a magnetic storage device, e.g., hard disk; floppy disk; magnetic strip(s); an optical disk (e.g., compact disk (CD), a digital video disc (DVD), a Blu-ray Disc™ (BD)); a smart card; a flash memory device (e.g., card, stick, key drive); and/or a virtual device that emulates a storage device and/or any of the above computer-readable media. Of course, those skilled in the art will recognize many modifications can be made to this configuration without departing from the scope or spirit of the various embodiments.

Disclosed embodiments and/or aspects should neither be presumed to be exclusive of other disclosed embodiments and/or aspects, nor should a device and/or structure be presumed to be exclusive to its depicted element in an example embodiment or embodiments of this disclosure, unless where clear from context to the contrary. The scope of the disclosure is generally intended to encompass modifications of depicted embodiments with additions from other depicted embodiments, where suitable, interoperability among or between depicted embodiments, where suitable, as well as addition of a component(s) from one embodiment(s) within another or subtraction of a component(s) from any depicted embodiment, where suitable, aggregation of elements (or embodiments) into a single device achieving aggregate functionality, where suitable, or distribution of functionality of a single device into multiple device, where suitable. In addition, incorporation, combination or modification of devices or elements (e.g., components) depicted herein or modified as stated above with devices, structures, or subsets thereof not explicitly depicted herein but known in the art or made evident to one with ordinary skill in the art through the context disclosed herein are also considered within the scope of the present disclosure.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the subject matter has been described herein in connection with various embodiments and corresponding FIGs., where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A system, comprising:
a processor; and
a memory that stores executable instructions that, when executed by the processor, facilitate performance of operations, comprising:
employing a model to identify a normal state or an anomalous state of a defined entity, wherein the model is trained on a first set of variables that are constrained by a second set of variables, wherein the first set of variables defines a normality and an anomaly of the defined entity, and wherein the second set of variables characterizes elements of the defined entity; and
transforming the second set of variables into a derivative representation that comprises the first set of variables, wherein the transforming comprises grouping elements of the defined entity based on a similarity function that is based on a pairwise similarity that comprises variables of different natures, and wherein the variables of different natures comprise configuration variables of the elements of the defined entity and conditions of usage variables of the elements of the defined entity.

2. The system of claim 1, wherein the pairwise similarity is between the elements of the defined entity, and wherein the pairwise similarity is based on combining the variables of different natures of the second set of variables into a single weighted similarity function.

3. The system of claim 1, wherein the operations further comprise:
prior to the employing, using machine learning to train the model based on the first set of variables that are constrained by the second set of variables, wherein the model is trained to at least a defined level of confidence.

4. The system of claim 1, wherein the operations further comprise:
detecting an anomaly of the defined entity based on the first set of variables, wherein the second set of variables provides context for a definition of normality and a detection of anomalies associated with the defined entity.

5. The system of claim 4, wherein the operations further comprise:
prior to the detecting the anomaly, constraining the first set of variables based on the derivative representation of the second set of variables.

6. The system of claim 1, wherein the operations further comprise:
assessing the first set of variables associated with a normal behavior to a group to which the first set of variables belong; and
classifying a test sample as normal or anomalous based on the assessing.

7. The system of claim 6, wherein the first set of variables comprise performance variables.

8. The system of claim 1, wherein the defined entity is a storage system, and wherein the first set of variables and the second set of variables are telemetry data variables of the storage system.

9. A method, comprising:
employing, by a system comprising a processor, a model, trained on a first set of variables that are constrained by a second set of variables, to identify expected parameters and unexpected parameters associated with a defined entity, wherein the first set of variables define a normality of the defined entity, and wherein the second set of variables characterize elements of the defined entity;
transforming, by the system, the second set of variables into a representation that comprises the first set of variables, and
combining, by the system, variables of different natures of the second set of variables into a single weighted similarity function, resulting in a pairwise similarity, and wherein the single weighted similarity function is based on the pairwise similarity between the elements of the defined entity.

10. The method of claim 9, wherein the variables of different natures comprise configuration variables of the elements of the defined entity and conditions of usage variables of the elements of the defined entity.

11. The method of claim 9, further comprising:
prior to the employing, training, by the system, the model using the first set of variables that are constrained by the second set of variables, wherein the training comprises employing machine learning, and wherein the model is trained to at least a defined level of confidence.

12. The method of claim 9, further comprising:
performing, by the system, anomaly detection of the defined entity based on the first set of variables, wherein the first set of variables provide context for a definition of normality and a detection of anomalies associated with the defined entity.

13. The system of claim 9, wherein the defined entity is a data center, and wherein the first set of variables and the second set of variables are telemetry data of the data center.

14. The system of claim 9, wherein the transforming the second set of variables comprises constraining the first set of variables based on a derivative representation of the second set of variables.

15. The system of claim 14, further comprising:
evaluating, by the system, performance variables associated with normal behavior of the defined entity to a group to which the second set of variables belong; and
classifying, by the system, a test sample as normal or anomalous based on a result of the evaluating.

16. The system of claim 14, wherein the transforming the second set of variables comprises grouping elements of the defined entity based on a similarity function.

17. A non-transitory machine-readable medium, comprising executable instructions that, when executed by a processor, facilitate performance of operations, comprising:
employing a model to identify a normal state or an anomalous state of a defined entity, wherein the model is trained on a first group of variables that are constrained by a second group of variables, wherein the first group of variables defines a normality and an anomaly of the defined entity, and wherein the second group of variables characterizes elements of the defined entity;
transforming the second group of variables associated with the defined entity into a derivative representation that comprises the first group of variables for the defined entity; and
grouping elements of the defined entity based on a similarity function, wherein the similarity function comprises variables of different natures, and wherein the variables of different natures comprise configuration variables of the elements of the defined entity and conditions of usage variables of the elements of the defined entity.

18. The non-transitory machine-readable medium of claim 17, wherein the similarity function is based on a pairwise similarity between the elements of the defined entity, and wherein the pairwise similarity is based on a combination of variables of different natures of the second group of variables into a single weighted similarity function.

19. The non-transitory machine-readable medium of claim 17, wherein the operations further comprise:
detecting an anomaly of the defined entity based on the first group of variables, wherein the second group of variables provides context for a definition of normality and a detection of anomalies associated with the defined entity.

20. The non-transitory machine-readable medium of claim 17, wherein the operations further comprise:
- assessing the first group of variables associated with the normality to a group to which the first group of variables belong, and
- classifying a test sample as normal or anomalous based on the assessing.

\* \* \* \* \*